(12) United States Patent
Zafar et al.

(10) Patent No.: US 10,830,725 B2
(45) Date of Patent: Nov. 10, 2020

(54) ELECTRONIC CHEMICAL SENSOR

(71) Applicant: International Business Machines Corporation, Armonk, NY (US)

(72) Inventors: Sufi Zafar, Briarcliff Manor, NY (US); Giulia Prone, Turin (IT)

(73) Assignee: International Business Machines Corporation, Armonk, NY (US)

( * ) Notice: Subject to any disclaimer, the term of this patent is extended or adjusted under 35 U.S.C. 154(b) by 80 days.

(21) Appl. No.: 16/186,977

(22) Filed: Nov. 12, 2018

(65) Prior Publication Data

US 2020/0150073 A1   May 14, 2020

(51) Int. Cl.
*G01N 27/30* (2006.01)
*G01N 27/414* (2006.01)

(52) U.S. Cl.
CPC ......... *G01N 27/301* (2013.01); *G01N 27/302* (2013.01); *G01N 27/414* (2013.01)

(58) Field of Classification Search
CPC ... G01N 27/301; G01N 27/302; G01N 27/333
See application file for complete search history.

(56) References Cited

U.S. PATENT DOCUMENTS

| | | | |
|---|---|---|---|
| 3,810,828 A * | 5/1974 | Lindholm | G01N 27/301 204/435 |
| 5,110,441 A | 5/1992 | Kinlen et al. | |
| 5,497,091 A | 3/1996 | Bratton et al. | |
| 6,356,830 B1 | 3/2002 | Adamchuck et al. | |

(Continued)

FOREIGN PATENT DOCUMENTS

| | | | | |
|---|---|---|---|---|
| CN | 201069429 Y | * | 6/2008 | ............ G01N 17/02 |
| CN | 202255460 U | | 5/2012 | |

(Continued)

OTHER PUBLICATIONS

EPO computer-generated English language translation of the Description section of CN 201069429 Y (Year: 2008).*
EPO computer-generated English language translation of the Description section of CN 207600996 U (Year: 2018).*

(Continued)

*Primary Examiner* — Alexander S Noguerola
(74) *Attorney, Agent, or Firm* — Christopher M. Pignato

(57) ABSTRACT

Devices, systems, methods and products for measuring concentrations of analytes in-situ, including concentrations of ions, proteins, DNA, and, RNA in a variety of mediums including solutions, suspensions, soils, slurries, biological fluids and living organic material such as agricultural crops. Embodiments of the disclosed inventions measure analyte concentration in-situ without clogging reference electrodes, leaking reference solution or having to dilute a medium prior to taking the analyte measurements. In-situ analyte measurements are made without clogging reference electrodes using a combination of solid-state sensors connected to a transducer, a reference electrode enclosed by a non-porous enclosure and a metallic plug extending from the interior cavity of the non-porous enclosure outwardly exterior to the non-porous enclosure, contacting the medium being measured. Automation of analyte measurements are implemented by combining computer systems, computer networks to remotely measure and monitor the analyte present in multiple mediums using sensors placed in a variable number of locations.

25 Claims, 20 Drawing Sheets

(56) References Cited

U.S. PATENT DOCUMENTS

| | | | |
|---|---|---|---|
| 8,444,937 | B2 | 5/2013 | Tuli et al. |
| 9,651,514 | B2 | 5/2017 | Soccol et al. |
| 9,806,151 | B2 * | 10/2017 | Ning ............... H01L 29/737 |
| 9,863,925 | B2 | 1/2018 | Gerber-Siff et al. |
| 2002/0016005 | A1 | 2/2002 | Campbell et al. |
| 2003/0132755 | A1 | 7/2003 | Feng et al. |
| 2011/0308303 | A1 | 12/2011 | Omoda |
| 2015/0346144 | A1 | 12/2015 | Lee et al. |

FOREIGN PATENT DOCUMENTS

| | | | | |
|---|---|---|---|---|
| CN | 207600996 U | * | 7/2018 | ............. G01N 27/22 |
| WO | 9853312 A1 | | 11/1998 | |

OTHER PUBLICATIONS

Schirrmann et al., "Soil pH Mapping with an on-the-Go Sensor", Sensors 2011, Received: Nov. 11, 2010; in revised form: Dec. 23, 2010/Accepted: Dec. 29, 2010/Published: Jan. 7, 2011, doi:10.3390/s110100573, © 2011 by the authors; licensee MDPI, Basel, Switzerland, pp. 573-598.

Zafar et al., "Comparison between Field Effect Transistors and Bipolar Junction Transistors as Transducers in Electrochemical Sensors", Scientific Reports 7, Article No. 41430 (2017), Published: Jan. 30, 2017, 27 pages, <https://www.nature.com/articles/srep41430#f2.

Zafar et al., "A comparison between bipolar transistor and nanowire field effect transistor biosensors", Appl. Phys. Lett. 106, 063701 (2015), Published Online: Feb. 12, 2015 Accepted: Jan. 2015, 24 pages, <https://aip.scitation.org/doi/10.1063/1.4907611>.

* cited by examiner

ELECTRONIC CHEMICAL SENSOR

TECHNICAL FIELD

The present invention relates generally to the field of electronic sensors, and more particularly to sensors for measuring the concentration of analytes in-situ from a solid medium such as soil.

BACKGROUND

Soil pH generally refers to the degree of soil acidity or alkalinity. In mathematical terms, pH is a −log 10 measurement of the concentration of hydrogen ions (H+) present in a solution of soil. The pH scale is measured from 0 to 14, with a pH of approximately 7 being considered neutral. A pH measurement of less than 7 is considered acidic while a pH of greater than 7 is considered basic. Commonly, the closer a soil solution is to 0, the more acidic the soil solution is due to the higher the concentration of H+ ions present in the soil. Conversely, pH measurements greater than 7 indicate that a soil solution is more basic due a lower concentration of hydrogen ions present in the soil solution.

Sources of H+ ions in a soil solution include the presence of carbonic acid ($H_2CO_3$) produced from carbon dioxide ($CO_2$) released by decomposing organic matter and root respiration. Other sources of H+ ions may be present in the soil due to root release, reactions of aluminum ions ($Al^{+3}$) with water, nitrification of ammonium from fertilizers and organic matter mineralization, reaction of sulfur compounds, rainwater, and acid rain. The pH differences in soils may be quite variable. Certain soil compositions may comprise a higher natural buffering capacity and therefore be more resistant to decreases in pH. Soil pH is important because pH affects the soil's physical, chemical and biological properties as well as plant growth. The nutrition, growth and yields of most crops are observable as a function of pH. Crop yields generally decrease in soils with a low pH and rise as the pH of soils increase, up to an optimal level, typically around a neutral to alkaline pH.

SUMMARY

A first embodiment of the present disclosure provides a device comprising: a transducer encased within a moisture-proof enclosure; a sensing surface electrically connected to the transducer, the sensing surface extending exterior to the moisture-proof enclosure and is inserted into the test medium wherein the reference electrode comprises a sealed, non-porous enclosure, a buffer solution encased within the non-porous enclosure, a wire submerged in the buffer solution and a metallic plug partially enclosed within the non-porous enclosure wherein said metallic plug partially extends exterior to the non-porous enclosure.

A second embodiment of the present disclosure provides a device comprising: a reference electrode having a sealed, non-porous enclosure, a reference solution encased within the non-porous enclosure, a wire submerged in the reference solution and a metallic plug partially enclosed within the non-porous enclosure, wherein said metallic plug partially extends exterior to the non-porous enclosure.

A third embodiment of the present disclosure provides a method for measuring analyte concentration comprising the steps of: connecting, a base of a bipolar junction transistor (BJT) encased in a moisture-proof enclosure to a sensing surface extending exterior to the moisture-proof enclosure; inserting, the sensing surface and a metallic plug of a reference electrode into a plurality of calibration solutions, each having a known analyte concentration, wherein said reference electrode comprises a non-porous enclosure, a buffer solution encased within the non-porous enclosure, a wire submerged in a buffer solution and the metallic plug is partially extends exterior to the non-porous enclosure; measuring an electrical current outputted from a collector ($I_c$) of the BJT as a function of a change in a difference between a voltage applied to the reference electrode ($V_B$) and a voltage applied to an emitter ($V_E$) of the BJT, wherein the $V_B$ is 0 volts (V) and $V_E$ is <0V, for each of the plurality of calibration solutions; generating a transference curve plotting $I_c$ as a function of the change in ($V_B - V_E$) (hereinafter "$V_{BE}$") for each of the plurality of calibration solutions; creating a calibration curve plotting $V_{BE}$ at a selected $I_c$ for each of the plurality of calibration solutions as a function of the known analyte concentration of each of the plurality of calibration solutions; measuring the $I_c$ of the substance of unknown analyte concentration outputted at the collector of the BJT; and plotting the $V_{BE}$ of the substance of unknown analyte concentration on the calibration curve at the selected $I_C$ used to create the calibration curve.

A fourth embodiment of the present disclosure provides a computer system comprising: a processor; a bipolar junction transistor (BJT) electrically coupled to the processor, said transducer is encased within a moisture-proof enclosure; a sensing surface electrically connected to the BJT, the sensing surface extending exterior to the moisture-proof enclosure; a reference electrode electrically connected to the BJT, wherein the reference electrode comprises a non-porous enclosure, a buffer solution encased within the non-porous enclosure, a wire submerged the buffer solution and a metallic plug partially enclosed within the non-porous enclosure and said metallic plug extending exterior to the non-porous enclosure; and a computer-readable storage media coupled to a processor, wherein the computer readable storage media contains program instructions executing a computer-implemented method comprising the steps of: measuring an electrical current outputted from a collector ($I_c$) of the BJT as a function of a change in a difference between a voltage applied to the reference electrode ($V_B$) and a voltage applied to an emitter ($V_E$) of the BJT, wherein the $V_B$ is 0 volts (V) and $V_E$ is <0V, for each of a plurality of calibration solutions; generating a transference curve comparing $I_c$ as a function of the change in ($V_B - V_E$) (hereinafter "$V_{BE}$") for each of the plurality of calibration solutions; creating a calibration curve plotting $V_{BE}$ at a selected $I_c$ for each of the plurality of calibration solutions as a function of a known analyte concentration of each of the plurality of calibration solutions; measuring the $I_c$ of the substance of unknown analyte concentration outputted at the collector of the BJT; and plotting the $V_{BE}$ of the substance of unknown analyte concentration at the selected $I_c$ used to create the calibration curve.

A fifth embodiment of the present disclosure provides a computer program product comprising: one or more computer readable storage media having computer-readable program instructions stored on the one or more computer readable storage media, said program instructions executes a computer-implemented method comprising the steps of: measuring an electrical current outputted from a collector ($I_c$) of the BJT as a function of a change in a difference between a voltage applied to a base ($V_B$) of the BJT and a voltage applied to an emitter ($V_E$) of the BJT, wherein the base is connected to a sensing surface and a reference electrode, said sensing surface and a metallic plug partially extending from a non-porous enclosure of the reference electrode are inserted into each of a plurality of calibration solutions, and $V_B$ is 0 volts (V) and $V_E$ is <0V; generating a transference curve comparing $I_c$ as a function of the change in ($V_B-V_E$) (hereinafter "$V_{BE}$") for each of the plurality of calibration solutions; creating a calibration curve plotting $V_{BE}$ at a selected $I_c$ for each of the plurality of calibration solutions as a function of a known analyte concentration of each of the plurality of calibration solutions; measuring the $I_c$ of the substance of unknown analyte concentration outputted at the collector of the BJT; and plotting the $V_{BE}$ of the substance of unknown analyte concentration at the selected $I_c$ used to create the calibration curve.

DETAILED DESCRIPTION

Overview

Figure 1:
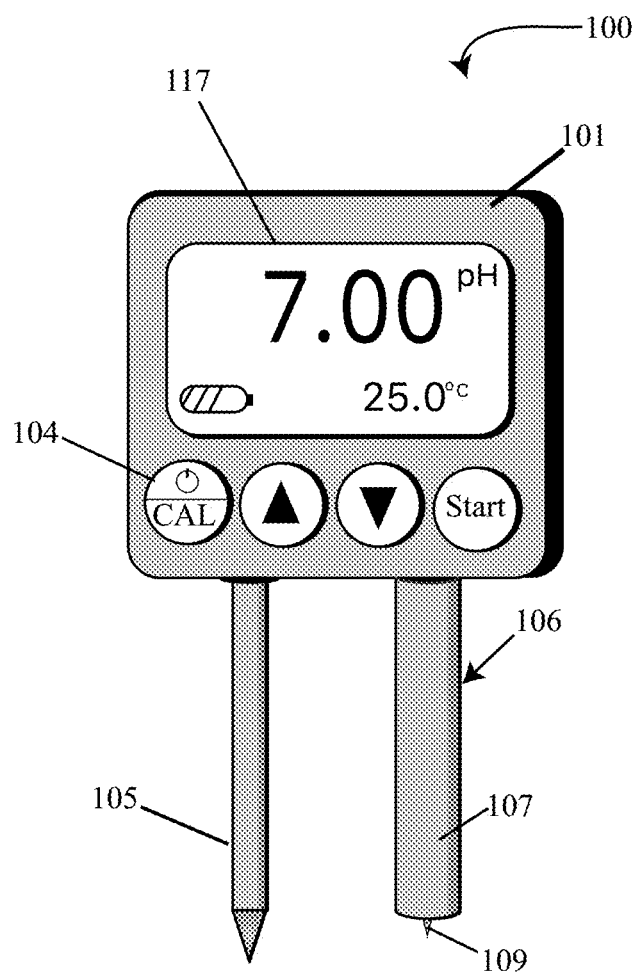
FIG. 1 illustrates a front view of an embodiment of a measuring device, in accordance with the present disclosure.

Embodiments of the present disclosure recognize that currently available electronic and electronic-chemical sensors lack the ability to directly measure analytes in situ from soil and other solid mediums. The term "analyte" may refer to any chemical substance that may be the subject of a chemical analysis. Existing devices are unable to be inserted into various mediums, such as soil, slurries, suspensions and some biological fluids, due to the structure of the commercially available reference electrodes integrated into the measuring devices. The reference electrodes of currently available measuring devices are prone to clogging as well as prone to leaking buffer solution over time due to the use of a porous membrane as part of the enclosure for the reference electrode. The clogged and/or depleted reference electrodes become unusable and cannot measure the analytes of the samples being tested. Instead, currently available measuring devices rely on measuring samples by first creating a diluted solution comprising the analyte in a liquid (such as water) and measuring the concentration of the analyte in the diluted solution.

Embodiments of the measuring devices, methods, systems and computer program products of the present disclosure recognize the design flaws of currently available measuring devices and correct the design flaws of the reference electrodes to allow for direct measurements of analytes in situ. Embodiments of the present disclosure may comprise solid state sensors that measure the concentration of analytes in substances directly, that may normally clog a traditional reference electrode. For example, measuring pH and/or other ion concentrations of soil (i.e., nitrates and phosphates) in the ground and/or other solid substances and slurries directly, without clogging the reference electrode, leaking buffer solution, or relying on first preparing a solution. The measurements are performed in-situ by sealing the contents of the reference electrode using a non-porous enclosure to encase a reference solution, such as a buffer solution, and a wire submerged within the reference solution, instead using a porous membrane. A second wire or conductive material, referred to herein as a "metallic plug", may also be incorporated as part of the reference electrode. The metallic plug may be constructed out of titanium nitride, tungsten or other materials described herein and may pass through the sealed, non-porous enclosure of the reference electrode. Embodiments of the metallic plug may be partially submerged within the reference solution encased within the non-porous enclosure, and the metallic plug may partially extend outwardly from the non-porous enclosure.

During the calibration of the calibration solutions or while measuring a substance of unknown analyte concentration, the portion of the metallic plug exterior to the non-porous enclosure, may contact the calibration solution and/or test medium of unknown analyte concentration without allowing for the ions or biological materials being tested, such as proteins, RNA and DNA, to enter the non-porous enclosure of the reference electrode. The analytes of the test medium and reference solution inside the non-porous enclosure interact with the metallic plug's surface. Since the metallic plug's surface in contact with the reference solution is significantly larger than the metallic plug's surface in contact with test medium, the surface potential of the metallic plug may depend on the reference solution and may remain constant, irrespective of the test medium analyte interaction. Hence, the metallic plug's potential is independent of the analyte interaction of the test medium.

Embodiments of the present disclosure may achieve direct measurements of unknown analyte concentrations by connecting a transducer, such as a bipolar junction transistor (BJT) or a field effect transistor (FET) to a sensing surface and exposing the sensing surface and the reference electrode to a series of calibration solutions of known analyte concentration. By applying an increasing or constant voltage to the transducer and measuring a current outputted by the transducer, a transfer curve may be generated which plots the measured current being outputted as a function of the voltage applied to the transducer. The difference between the electrical potential at the sensing surface and the reference electrode may be amplified proportionally by applying a constant or variable voltage from a power source to one or more different portions of the transducer. As an amplification voltage is applied, the current output being measured may proportionally increase as well.

Embodiments of the measuring device may use the data generating the transfer curve to create a calibration curve of known measured voltage applied to the transducer at a fixed, consistent selected current, for each of the specific known analyte concentrations of each calibration solution. For example, the calibration curve can be generated by plotting an applied voltage to an output current of 1 Nano ampere (nA) for each of the calibration solutions as a function of the known analyte concentration of each calibration solution. In other examples, the selected current for creating the calibration curve can be less than 1 nA, or more than 1 nA so long as the selected current is consistent for each measurement. The resulting calibration curve may be subsequently used to plot measurements of the voltage differences for substances of unknown analyte concentration at a current output of 1 nA in order to find the analyte concentration of said unknown substance, thus allowing for identification of unknown analyte concentrations.

Measuring Device

Although certain embodiments are shown and described in detail, it should be understood that various changes and modifications may be made without departing from the scope of the appended claims. The scope of the present disclosure will in no way be limited to the number of constituting components, the materials thereof, the shapes thereof, the relative arrangement thereof, etc., and are disclosed simply as an example of embodiments of the present disclosure. A more complete understanding of the present embodiments and advantages thereof may be acquired by referring to the following description taken in conjunction with the accompanying drawings, in which like reference numbers indicate like features.

As a preface to the detailed description, it should be noted that, as used in this specification and the appended claims, the singular forms "a", "an" and "the" include plural referents, unless the context clearly dictates otherwise.

Referring to the drawings, FIG. 1 depicts an embodiment of a measuring device 100, capable of measuring the concentration of analytes present in one or more substances having an unknown analyte concentration. For example, the measuring device 100 may measure concentrations of analytes including but not limited to ions such as hydrogen ions, halides (such as chloride, fluoride, bromide, iodide), alkaline metals/ions thereof (lithium, sodium, potassium, rubidium, cesium, francium), alkaline earth metals/ions thereof (i.e., beryllium, magnesium, calcium, strontium, barium, radium) ions of transition metals/ions thereof residing in group 3 to 12 of the periodic table, metalloids and transition metal or metalloid compounds (i.e., ions and ionic compounds comprising for example, titanium, iron, cobalt, zinc, chromium, lead, mercury, tin, aluminum, etc.), nitrates, phosphates, amines and biological substances including proteins, RNA, and DNA.

In some embodiments, the concentration of hydrogen ions may be measured by the measuring device 100. Measuring the concentration of hydrogen ions may be referred to as measuring the pH of a substance, wherein hydrogen ions may be considered the analyte being measured. The term "pH" may refer to the −Log 10 molar concentration (expressed in moles/liter) of the hydrogen ions (H+). The pH scale may extend from approximately 0.00 to 14.00. Solutions and substances measured with a pH of approximately 7.00 may be considered a neutral pH, while solutions and substances less than 7.00 may be considered acidic (i.e. a higher concentration of H+ ions than OH− ions) while those above 7.00 may be considered basic (i.e. a higher concentration of OH− ions that H+ ions).

Embodiments of the measuring device 100 may include a moisture-proof or moisture resistant enclosure (simplified referred herein together or interchangeably throughout as a "moisture-proof enclosure 101") which may surround and/or protect one or more internal components, electronic circuitry, wiring, sensor connections, transducers and computer systems. Embodiments of the moisture-proof enclosure 101 may be any shape or size that may be needed to house each of the components stored inside the moisture-proof enclosure 101. It should be understood that the shape of the moisture-proof enclosure 101 depicted in FIGS. 1-6b should in no way be considered limited to the shape, size or features depicted. Embodiments of the moisture-proof enclosure 101 may be constructed out of any material that may provide sufficient protection to each of the components store within the moisture-proof enclosure 101. For example, the moisture-proof enclosure 101 can be constructed out of plastic resins, glass or metals, including but not limited to high density polyethylene (HDPE), polyethylene terephthalate (PET), polypropylene, polystyrene, polyvinyl chloride (PVC), borosilicate glass, aluminosilicate glass, fused silica glass, tempered glass, steel, stainless steel, aluminum, iron, and alloys or combinations thereof.

Figure 2:
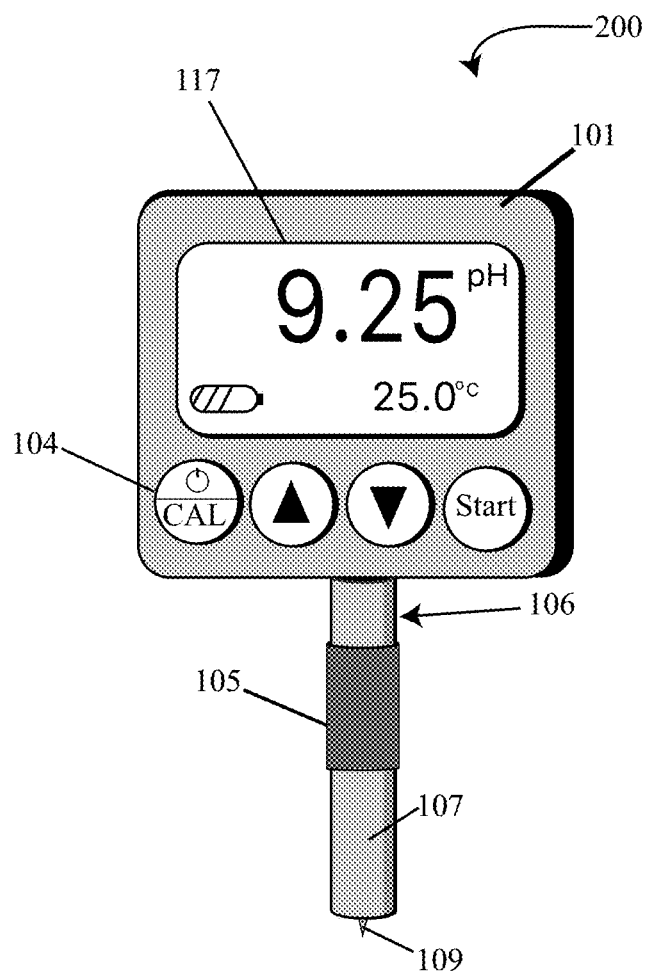
FIG. 2 illustrates a front view of an alternative embodiment of a measuring device in accordance with the present disclosure.
Figure 3:
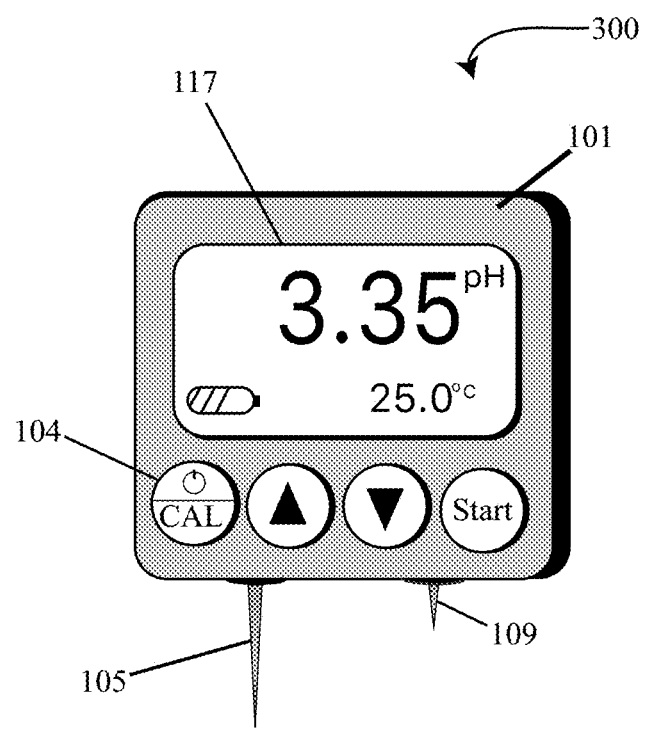
FIG. 3 illustrates a front view of a second alternative embodiment of a measuring device in accordance with the present disclosure.

Embodiments of the measuring device 100 may further comprise a control system 104 which may be accessible from the exterior of the moisture-proof enclosure 101 as shown in FIGS. 1-3 and may control, provide input, or make user-guided selections while operating the measuring device 100. The control system 104 may access computer systems, circuitry and sensor systems that may be housed within the moisture-proof enclosure 101. In some embodiments, the control system 104 may include buttons, dials, levers, switches, a keypad or other control inputs known or used by those skilled in the art. For example, one or more control inputs may select the type of analyte being measured by the measuring device 100, such as the concentration of hydrogen ions (pH) as shown in FIG. 1-3, alkaline metal ions, alkaline earth ions, transition metal ions, metalloid ions, halides, nitrogen containing compounds (nitrates and amines), phosphate containing compounds and biological substances such as proteins, RNA, and DNA. In alternative embodiments, the control system 104 may remotely access the systems and functions of the measuring device 100, for example, through an application loaded onto a smartphone or other computing device that is capable of sending signals remotely to the measuring device 100 (i.e. using Wi-Fi, Bluetooth, Zigbee, infrared, etc.). In alternative embodiments, the control system 104 may be integrated into a display 117, such as a touch screen display system.

Embodiments of the measuring device may further include a sensing surface 105 which may extend outwardly from the interior of the moisture-proof enclosure 101 and be exposed outside of the moisture-proof enclosure 101. Embodiments of the sensing surface 105 may be any shape and/or size. Embodiments of the sensing surface 105 may extend to any length or thickness that may be sufficient for obtaining a measurement of an analyte concentration of a substance. For example, the length of the sensing surface 105 may be approximately less than a quarter inch (6 mm), greater than a quarter inch (6 mm), greater than a half inch (12 mm), greater than 18 inches (457 mm), between approximately 0.25 (6 mm) to 18 inches (457 mm), 1 (25 mm) to 12 inches (305 mm), 3 (76 mm) to 8 inches (203 mm) and/or 4-6 inches (101-153 mm). Embodiments of the sensing surface 105 may be constructed out of any material or coated with any material that may be suitable for attracting analyte ions to exterior surface of the sensing surface 105. Embodiments of the sensing surface 105 may be constructed out of or coated with metals, metal oxides, metal nitrides (such as titanium nitride) and alloys thereof. For instance, embodiments of the sensing surface 105 may be constructed out of or coated with tin, lead, arsenic, antimony, bismuth, copper, silver, gold, zinc, titanium, mercury, tungsten, tantalum, rhenium, iron, nickel, osmium, rhodium, iridium, platinum, oxides thereof, nitrides thereof and alloys thereof.

The shape and dimension of the sensing surface 105 may vary from embodiment to embodiment. For example, in the exemplary embodiment of the measuring device 100, the sensing surface 105 may be constructed into an elongated or cylindrical shape which may include a pointed end. The inclusion of a pointed end on the sensing surface 105 may be useful for penetrating into a solid or semi-solid surface, such as a soil or slurry comprising one or more ions of an analyte which may be measured by the measuring device 100. In other embodiments of the sensing surface 105, the sensing surface 105 may be retractable or extendable in length. The control system 104 may be operated to initiate the extension of the sensing surface 105 at the point in time when the concentration of a substance's analyte or analyte of a calibration solution is ready to be measured.

In alternative embodiments such as the measuring device 300 shown in FIG. 3, the sensing surface 105 may be a sharp or skinny, needle-like protrusion that may extend outwardly from the moisture-proof enclosure 101. A sensing surface 105 that has a sharp, needle-like protrusion for a shape may be useful for penetrating through tough surfaces while measuring analyte concentration. For example, to penetrate through compacted soils, hard clays, organic tissues or the skin of fruits and vegetables. Moreover, sensing analyte concentrations in fruits and vegetables in embodiments such as measuring device 300, 300b may be useful for agricultural purposes, particularly for monitoring the optimal time for harvesting fruits and vegetables. Embodiments of the measuring device 300, 300b may be connected to a computing environment 700, 730 described below, which may continuously sample and record the analyte concentrations of the fruits, vegetables, and/or soil then compare the measured analyte concentrations with an optimal concentrations and recommend measures for the user to balance the analytes for optimal growing, harvesting and fertilizing.

In some embodiments of the sensing surface 105, such as the embodiment depicted by measuring device 200, 200b the sensing surface 105 may not protrude outwardly from the moisture-proof enclosure 101. As shown in FIG. 2, the sensing surface 105 may be exposed externally to the moisture-proof enclosure 101 by depositing or coating an exterior surface of the non-porous enclosure 107 of the reference electrode 106 with the sensing surface 105. As the reference electrode 106 is inserted into the substance being measured by the measuring device 200, the sensing surface 105 is also exposed to the substance being measured and may attract the analytes of the substance being measured to the sensing surface 105 deposited on the exterior surface of the non-porous enclosure 107.

Embodiments of the measuring device 100 may include a reference electrode 106. A reference electrode 106 may refer to an electrode with a stable or invariant electrical potential (independent of the analyte concentration in the test medium (403)) for which the electrical potential of the sensing surface 105 can be compared with. Embodiments of the reference electrode 106 as shown for example in FIG. 4a, may comprise a non-porous enclosure 107, a reference solution 413 such as a pH buffer solution disposed within a hollow interior cavity of the non-porous enclosure 107, a first metal wire 411 (referred hereinafter as "wire 411") submerged within the reference solution 413, and a second metal wire 109 of conductive material (referred hereinafter as "metallic plug 109") which may be partially submerged within the reference solution 413 and partially exposed to the environment outside of the non-porous enclosure 107. Embodiments of the wire 411 may be maintained at a constant voltage as described below (e.g. a voltage of 0V). Embodiments of the wire 411 and metallic plug 109 may be constructed out of the same materials in some instance, and dissimilar materials in alternative embodiments. For example, the wire 411 being maintained at a constant voltage can be a titanium nitride (TiN) while the metallic plug 109 may be constructed out of TiN as well, while in other embodiments, the metallic plug 109 may be constructed out of a tungsten material.

Embodiments of the non-porous enclosure 107 may encase one or more components of the reference electrode 106 and the non-porous enclosure 107 may extend from the moisture-proof enclosure 101. Embodiments of the non-porous enclosure of the reference electrode 106 may be constructed as an elongated tube or vessel which may house the wire 411, reference solution 413 and/or partially enclosed metallic plug 109 which may partially reside within the interior cavity of the non-porous enclosure 107 while simultaneously a portion of the metallic plug 109 may protrude from the non-porous enclosure 107 of the reference electrode 106. Embodiments of the non-porous enclosure 107 may be constructed out of any materials similar to the materials that may be used to construct the moisture-proof enclosure 101. For example, plastic resins, glass or metals, including but not limited to high density polyethylene (HDPE), polyethylene terephthalate (PET), polypropylene, polystyrene, polyvinyl chloride (PVC), borosilicate glass, aluminosilicate glass, fuse silica glass, tempered glass, steel, stainless steel, aluminum, iron, and alloys or combinations thereof. In the exemplary embodiment, the material used to construct the non-porous enclosure 107 may be selected which may be inert when coming in contact with the substance having an analyte concentration measured. Moreover, the materials selected for the construction of the non-porous enclosure 107 may also be selected based on the inertness relative to the reference wire 411, reference solution 413 and/or the metallic plug 109.

As shown in the embodiments of measuring device 100, 100b, 200, 200b the reference electrode 106 may extend outwardly from the moisture-proof enclosure 101, allowing for the exterior surface of the non-porous enclosure 107 and a portion of the metallic plug 109 to be directly placed in contact with the test substance 403 such as the soil depicted in FIG. 4a-5b. In alternative embodiments of the measuring device 300, 300b, one or more portions of the reference electrode 106 may be enclosed within the moisture-proof enclosure 101 of the measuring device 300. As shown in FIG. 3 and FIGS. 6a-6b, a portion of reference electrode 106 may be internalized into the moisture-proof enclosure 101, except for the portion of the metallic plug 109 which may be partially within the non-porous enclosure 107 and may partially extend outside of both the non-porous enclosure 107 and the moisture-proof enclosure 101 in order to make contact with a test substance 403, as shown in FIGS. 4a-5b or an organic test substance 603 derived from living matter such as the fruit depicted in FIGS. 6a-6b.

Embodiments of the non-porous enclosure 107 may include a hollow interior cavity which may be filled with a reference solution 413. In some embodiments, the reference solution 413 may be a buffer solution which may be described as a solution that resists changes to pH when acid or alkalis contact the buffer solution. Embodiments of the reference solution 413 may be an acidic buffer solution and/or an alkaline buffer solution. Acidic buffer solutions may be a buffer solution having a pH that may be less than 7. Embodiments of acidic buffer solutions may be made from a weak acid and a salt thereof. For example, a sodium salt, such as ethanoic acid and sodium ethanoate. Conversely, an alkaline buffer may be described as buffer solution having a pH greater than 7 and may be prepared from a weak base and one of the weak base's corresponding salts. For example, an ammonia solution and ammonium chloride.

Embodiments of the reference solution 413 may have a pH between approximately 5-10, 6-9 and/or 7-8. In the exemplary embodiment of the reference solution 413, a buffer solution may be prepared with a pH of between approximately 6-8. Examples of suitable reference solutions 413 that may be provided within the hollow interior cavity of the non-porous enclosure 107 may include, but are not limited to sodium acetate (a combination of acetic acid and sodium acetate), buffered saline (i.e. PBS, TBS, TNT, PBT), tris-HCl, citrate buffers (citric acid and sodium citrate), Sorensen's phosphate buffer, phosphate-citrate buffers, barbital buffers (sodium barbital and HCl), tris buffers such as disodium ethylene diamine tetraacetate (EDTA), tris-EDTA, STE (tris-NaCl-EDTA), glycine-NaOH buffers and any other buffer known or used by a person skilled in the art.

Embodiments of the wire 411 may be placed within the hollow cavity of the non-porous enclosure 107 and partially or fully submerged within the reference solution 413. Embodiments of the wire 411 may include materials that may be selected based on having a property of high conductivity and the ability to not leak from the non-porous enclosure 107 of the reference electrode 106. Examples of a suitable wire 411 material may include titanium nitride (TiN), a silver/silver-chloride (Ag/AgCl) wire in a NaCl or KCl solution, mercury/mercury-chloride (Hg/HgCl$_2$), or a platinum wire in an iodine/iodide solution. Additional types of reference wire 411 materials may include materials or coatings that are similar to the materials used for constructing or coating a sensing surface 105 and/or metallic plug 109. For example, the wire 411 may be constructed out of or coated with metals, metal oxides, metal nitrides (such as titanium nitride) and alloys thereof, including but not limited to tin, lead, arsenic, antimony, bismuth, copper, silver, gold, zinc, titanium, mercury, tungsten, tantalum, rhenium, iron, nickel, osmium, rhodium, iridium, platinum, oxides thereof, nitrides thereof and alloys thereof.

Embodiments of the reference electrode 106 may further include a metallic plug 109 which may be positioned partially within the non-porous enclosure 107 while simultaneously extending exterior to the non-porous enclosure 107. Embodiments of the metallic plug 109 may be partially exposed to the substance having an analyte concentration measured. Embodiments of the metallic plug 109 may be constructed out of any materials that may be used for constructing the sensing surface 105 and/or the wire 411. For example, the metallic plug 109 may be constructed out of or coated with metals, metal oxides, metal nitrides (such as titanium nitride) and alloys thereof, including but not limited to tin, lead, arsenic, antimony, bismuth, copper, silver, gold, zinc, titanium, mercury, tungsten, tantalum, rhenium, iron, nickel, osmium, rhodium, iridium, platinum, oxides thereof, nitrides thereof and alloys thereof.

Embodiments of the metallic plug 109 play a unique role in the measurement of the unknown analyte concentration of the substances being tested. The metallic plug 109 may remain partially in contact with substances being tested via the exposed end while also remaining partially submerged within the reference solution 413. The part of the metallic plug that is in contact with the reference solution 413 can be referred as the interior plug surface, whereas the part of the metallic plug that is in contact with test substance (403, 603) can be referred as the exterior surface of the metallic plug. The solid metallic plug prevents the analytes and other ions or biological substances from entering the reference solution 413 or making contact with the wire 411. Since the metallic plug 109 is in contact with two different substances (the test substance and reference solution 413), the surface potential of the metallic plug 109 is independent of the analytes in the test substance (403, 603) than the interior surface area of the metallic plug 109. Since the plug 109 is metallic, its surface potential is the same both inside and outside the enclosure 107. When the interior surface area is significantly larger than the exterior surface area of the metallic plug (i.e. at least 25 times larger) then the plug surface potential may be controlled by the reference solution and is independent of the analyte concentration of the test substance.

Embodiments of the metallic plug 109 integrated into the reference electrode 106 of the measuring device 100, may be any length and/or thickness. However, in some embodiments, the ratio between the surface area of the metallic plug 109 exposed to the test substance 403 and/or organic test substance 603 being tested for a concentration of an analyte and the surface area contained within the non-porous enclosure 107 may vary and/or contribute to the sensitivity of the metallic plug 109 to changes in analyte concentration. It may be desirable for the metallic plug 109 and the reference electrode 106 in general to have a low sensitivity to the changes in analyte concentration, for example, changes in pH.

Figure 15A:
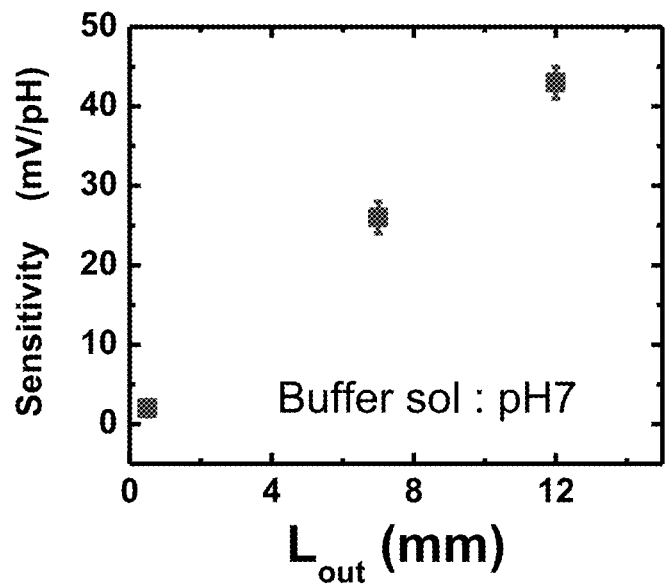
FIG. 15a depicts a graphical interpretation of experimental results where the proposed reference electrode sensitivity to analyte such as pH is measured. The proposed reference electrode showed no dependence on the analyte concentration. The measurements are performed using the proposed reference electrode as the sensing surface connected to the transducer and immersed in the test solution and a commercially available AgCl/Ag reference electrode. The pH sensitivity of the proposed reference electrode is measured as a function metallic plug exterior length; the reference solution is pH 7 buffer. The pH sensitivity of the proposed reference electrode is ~0 when the exterior surface area of the plug is >25 smaller that the plug interior surface area.

Referring to the drawings, FIG. 15a represents graphical interpretation of experiments performed by the inventors studying the effects of length and/or surface area of the metallic plug 109 exposed to a test substance 403 ($L_{out}$) on the sensitivity of the reference electrode 106 to pH changes. The proposed reference electrode showed no dependence on the analyte concentration. The measurements are performed using the proposed reference electrode as the sensing surface connected to the transducer and immersed in the test solution and a commercially available AgCl/Ag reference electrode. The pH sensitivity of the proposed reference electrode is measured as a function metallic plug exterior length; the reference solution is pH 7 buffer. The pH sensitivity of the proposed reference electrode is ~0 when the exterior surface area of the plug is >25 smaller that the plug interior surface area.

The experiment performed measured the changes in mV/pH at a constant current, selected by the inventors of 1 Nano ampere, as a function of $L_{out}$ measured at 0.5 mm, 7 mm and 12 mm using a reference solution 413 having a pH of 7. As demonstrated by the results, sensitivity of the metallic plug 109 to changes in pH increased as the length, $L_{out}$ (and thus the surface area) of the metallic plug 109 exposed to the test substance increased. As a result of the experiment described in FIG. 15a, embodiments of the metallic plug 109 may have length or surface area extending outwardly from the non-porous enclosure 107, exposed to the test substance 403, that is less than the length or surface area of the metallic plug 109 residing within the non-porous enclosure 107 ($L_{in}$). In one or more exemplary embodiments, the surface area of the metallic plug 109 may be >25 times smaller than the $L_{in}$ of the metallic plug 109. In alternative embodiments, the $L_{out}$ may be >2 times, >5 times, >10 times, >15 times, >20 times or >25 times smaller than the surface area of the metallic plug 109 encased within the non-porous enclosure 107.

Figure 15B:
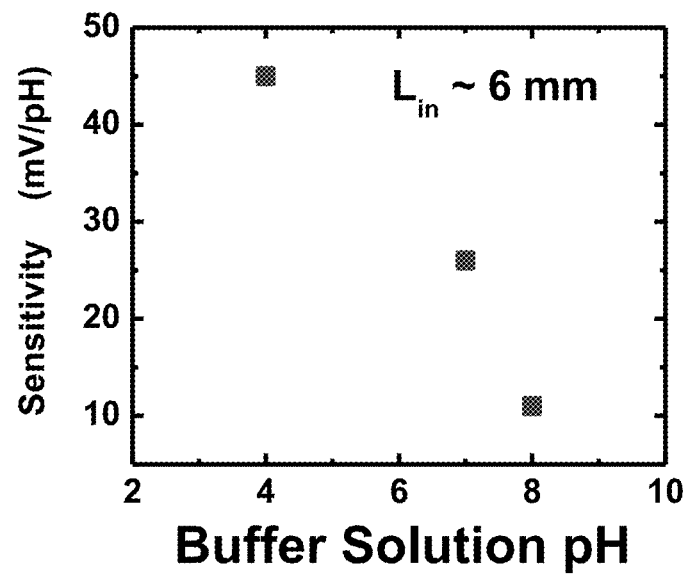
FIG. 15b depicts a graphical interpretation of experimental results describing the effects pH of a buffer solution on the sensitivity of the metallic plug to changes in analyte concentration of the test substance.

Embodiments of the metallic plug 109 may also be selected based on sensitivity to changes in the analyte being measured based on the concentration of the analyte of the reference solution 413. For example, in experiments performed by the inventors, the inventors measured the effects on the sensitivity toward changes in pH of a metallic plug 109 constructed out of tungsten using a reference solution 413 having a known pH. During the experiment, the $L_{in}$ of the metallic plug was approximately 6 mm. Reference solutions 413 were tested at a pH of approximately 4, 7, and 8 and the sensitivity measured in mV/pH at a current output of 1 nA. As demonstrated by the data shown in FIG. 15b, the sensitivity of the tungsten metallic plug 109 decreased as the pH of the reference solution 413 approached an optimal pH of approximately 8.0.

Referring to the drawings, FIGS. 4a-6b depict a schematic view of the embodiments of measuring device 100, 200, 300 shown in FIGS. 1-3, discussed above. Embodiments of the measuring device 100, 200, 300 may include a transducer enclosed within the moisture-proof enclosure 101 of the measuring device 100, 200 300. Embodiments of the transducer may be a bipolar junction transistor (BJT), as depicted in embodiments 100, 200, 300 of FIGS. 4a, 5a, 6a or a field effect transistor (FET) as depicted in embodiments 100b, 200b, 300b of FIGS. 4b, 5b, 6b. The transducer (whether BJT or FET) works with the sensing surface 105. The sensing surface 105 has a selective affinity for the analyte being measured (i.e., in the case of pH, H+ ions) while the transducer converts the interaction between the sensing surface 105 and the analyte into a readable electric signal.

A BJT may be described as a semiconductor device constructed onto a substrate 410 such as a silicon substrate 410 or doped silicon substrate 410. The BJT may include three doped semiconductor regions, wherein each region may have a terminal 423. These regions of the BJT may be referred to as a base 417, an emitter 419 and a collector 421. The construction of the BJT consists of two PN-junctions which form at the base-emitter junction and the base-collector junction. Embodiments of a BJT transducer may be an N-P-N or P-N-P configuration. Whether N-P-N or P-N-P, a BJT may include the same portions and operate the same except for the polarity of a power supply connected to the transducer circuit. BJT devices may regulate and control an amount of electrical current flowing through the BJT from the emitter 419 to the collector 421 terminals 423 in proportion to the amount of biasing voltage being applied to the base 417 terminal. A small current flowing into the base 417 may control a much larger collector current ($I_c$) being outputted at the collector 421.

Figure 4A:
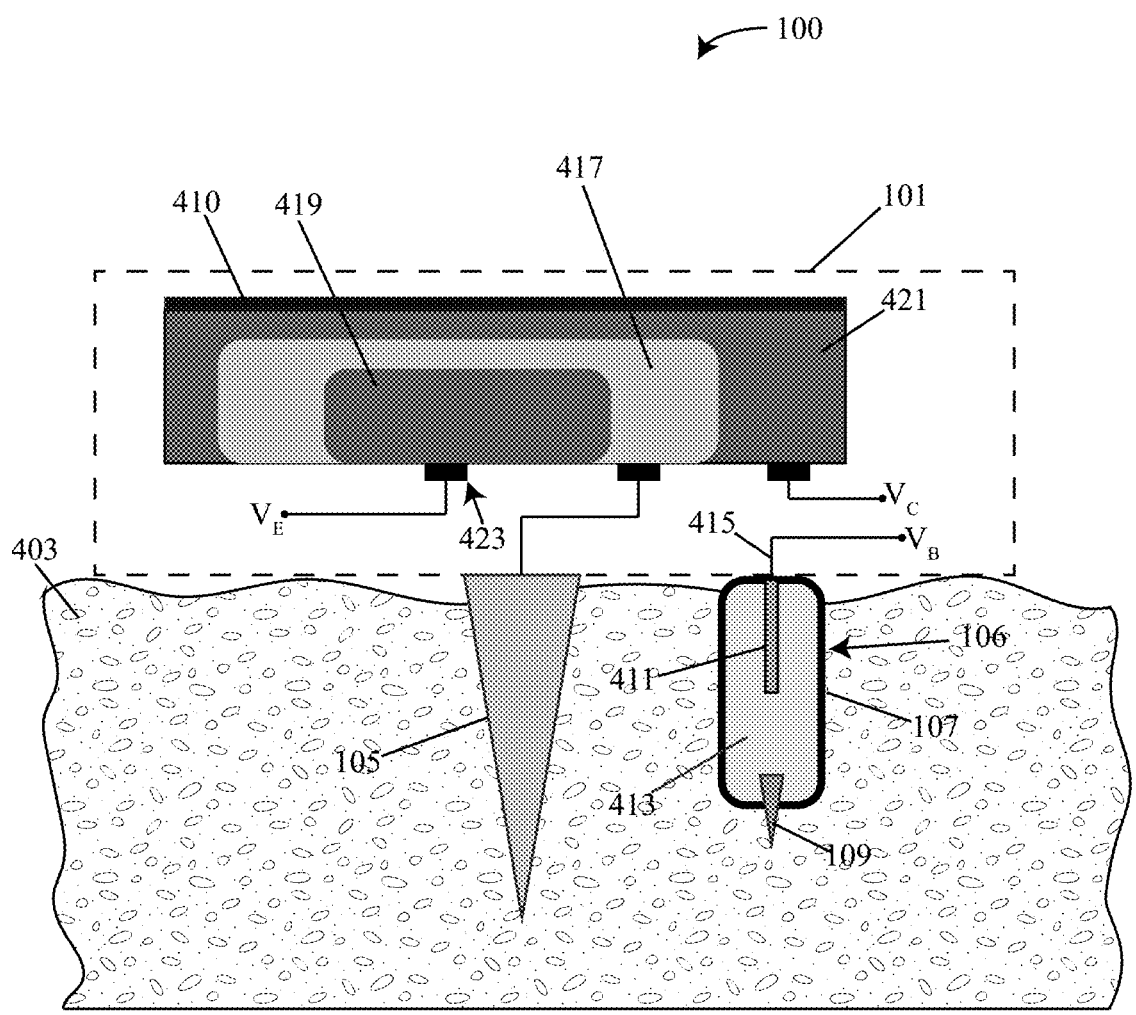
FIG. 4a depicts a schematic view of an embodiment of a sensor comprising a bipolar junction transistor (BJT)
Figure 5A:
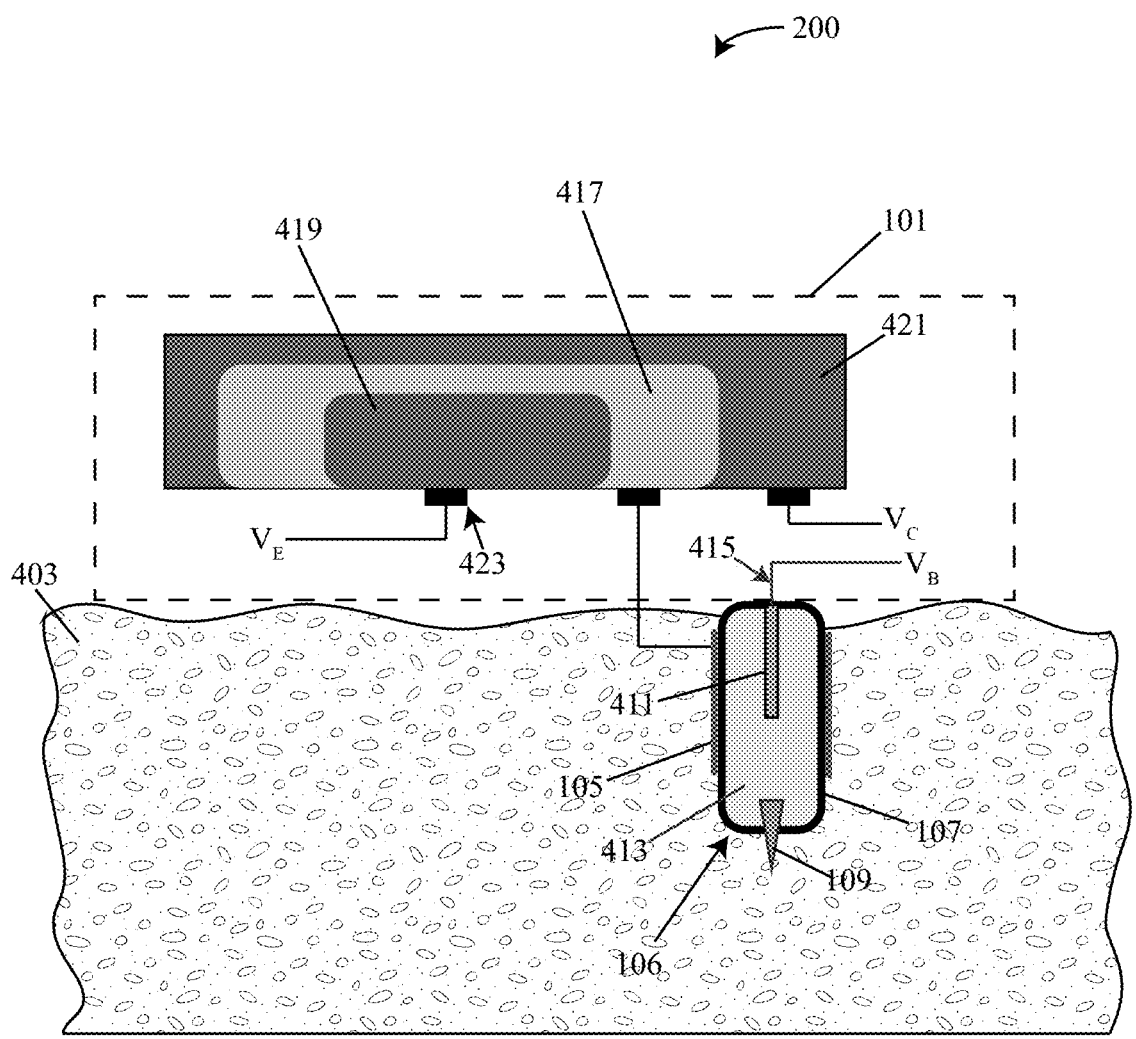
FIG. 5a depicts a schematic view of an alternative embodiment of a sensor comprising a BJT.
Figure 6A:
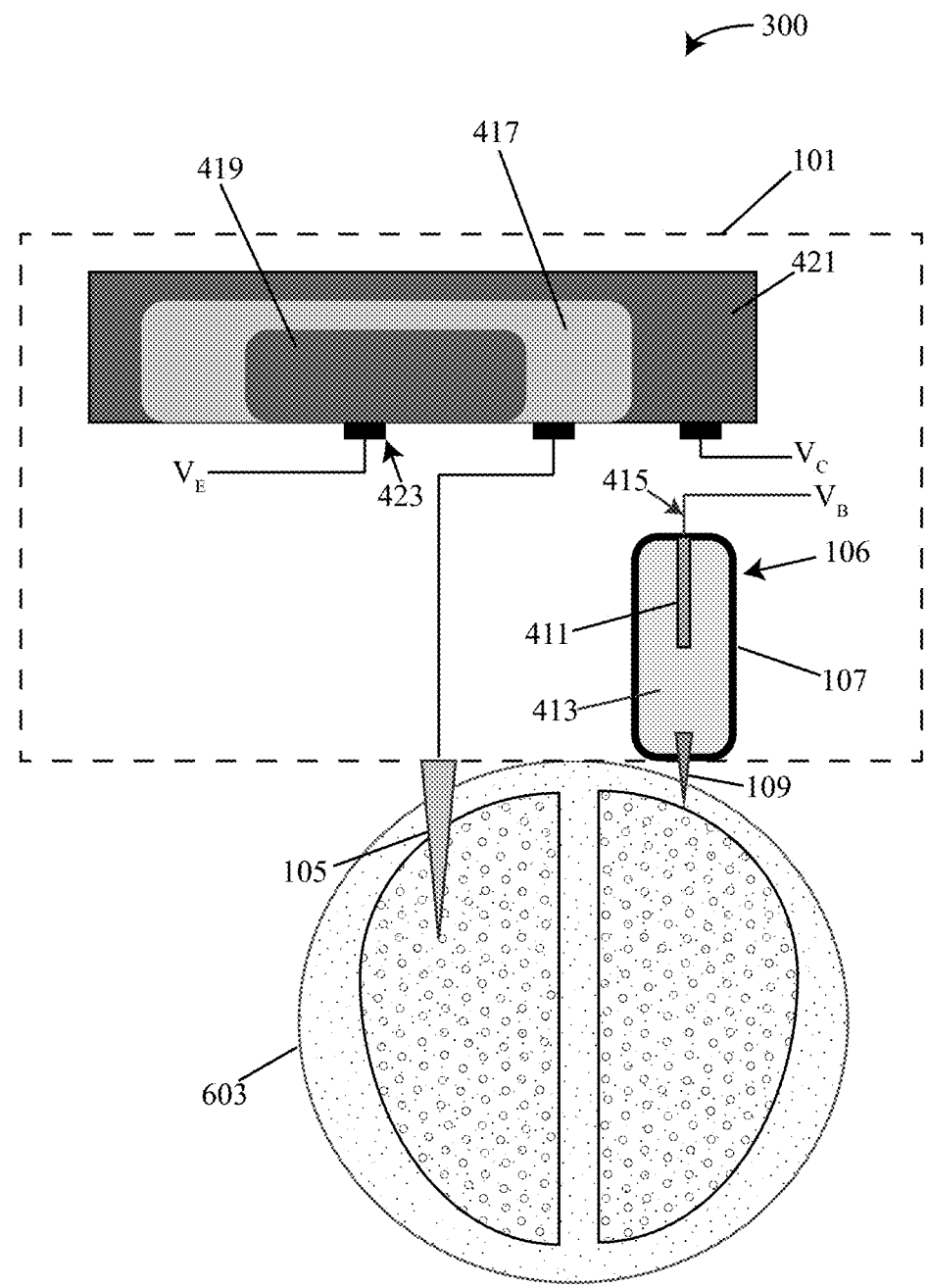
FIG. 6a depicts a schematic view of a second alternative embodiment of a sensor comprising a BJT.
Figure 6B:
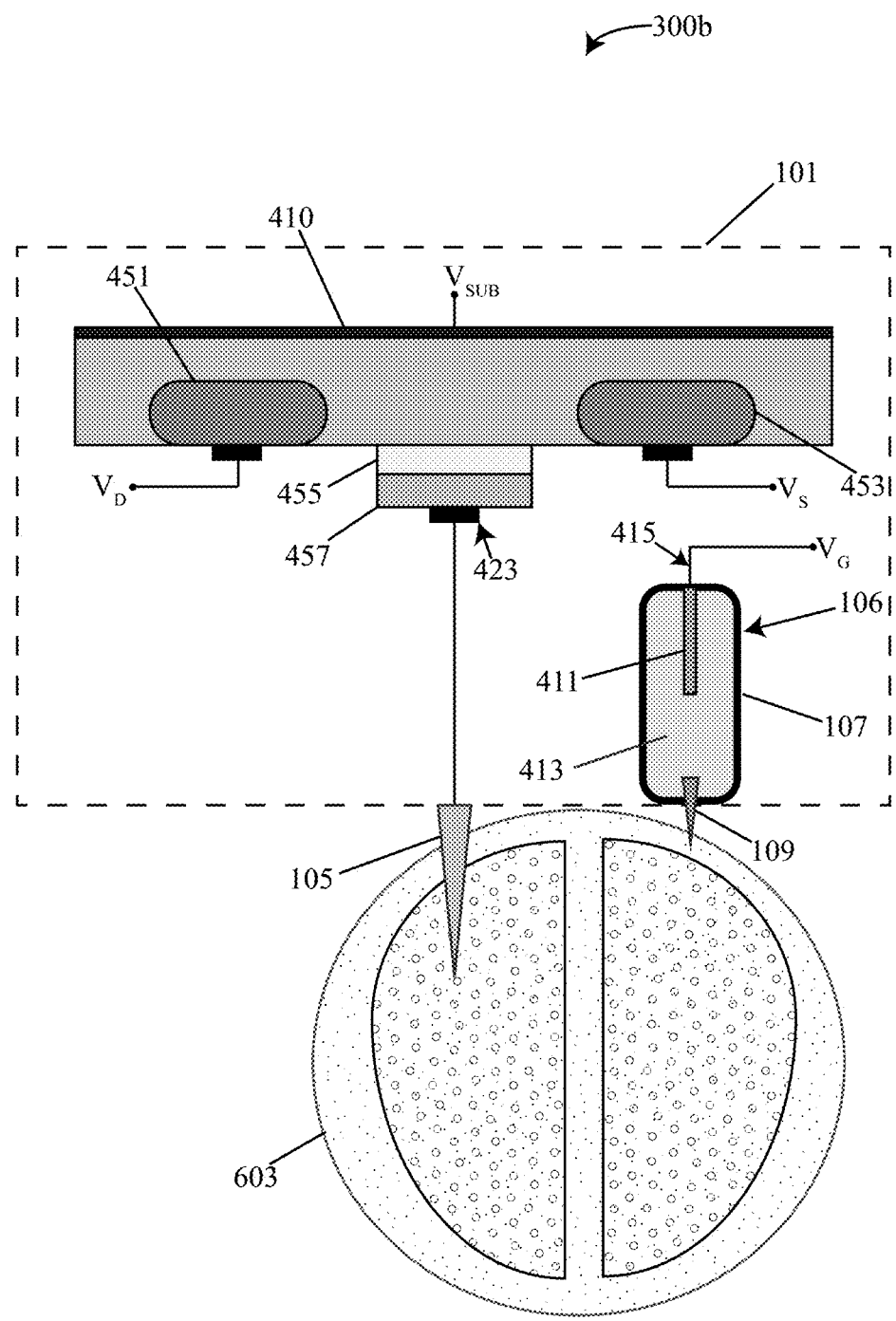
FIG. 6b depicts a schematic view of a second alternative embodiment of a sensor comprising a FET.

The exemplary embodiments of the BJT transducer depicted in FIGS. 4a, 5a, 6a may be an NPN BJT with a base 417 electrically connected to a sensing surface 105. The sensing surface 105 may be placed into contact with a calibration solution or a test substance 403 such as a soil, slurry, biological fluid or an organic test substance 603 such as fruits, vegetables or other living matter as shown in FIGS. 4a, 5a, 6a. The BJT device may be fabricated using standard silicon processing technology, as known or understood by individuals skilled in the art. In the exemplary embodiments of the BJT, voltages may be applied at the emitter 419 ($V_E$), the collector 421 ($V_C$) and the wire 411 ($V_B$) connected to a power supply via an electrically conductive material 415. The current ($I_C$) of the collector 421 may be used as the sensing signal outputted at the collector 421. Each of the sensing measurements of $I_C$ may be made at the collector 421 by applying a constant voltage applied to the base 417 and the collector 421. In the exemplary embodiments the voltage applied to the base $V_B$ and $V_C$ may be 0V. A voltage may also be applied at the emitter 419, $V_E$, which may be either varied or set to a fixed value. The voltage $V_E$ applied to an emitter 419 in an NPN configuration may be less than 0V (i.e. a negative voltage). Conversely, in embodiments where the BJT is a PNP configuration, the voltage $V_E$ applied to the emitter may be greater than 0V.

As mentioned above, the collector 421 current, $I_C$, may be used as the sensing signal. The transfer curve of a BJT sensor set in an active mode may be governed by the Ebers-Moll equation referenced as equation (1) as shown below. Active mode may refer to a mode of operation between a cutoff mode, wherein the BJT may be fully-on or off (like an open switch) and saturated mode, when the BJT is fully conductive, passing as much current through the collector 421 as a power supply and load will allow. In an active mode, the current passing through the collector 421 is throttled between the cutoff and saturation modes.

$$I_C = I_o \exp\{q(V_B + \Psi_s - I_B R - V_E)/kT\} \quad \text{Equation (1):}$$

In the above equation (1), $\Psi_s$ is the sensing surface 105 potential, $I_o$ is a constant dependent upon BJT device design parameters, k is the Boltzmann constants, T is the temperature in Kelvin and q is the electronic charge. As mentioned above, $V_E$ may refer to the voltage applied at the emitter 419 and $V_B$ may be the base 417 voltage applied at the reference electrode 106 at wire 411. $I_B$ is the base 417 current flowing through the substance being measured, such as a calibration solution, test substance 403 or organic test substance 603 and R is the resistance being provided by the substance being measured. The $I_B \cdot R$ can be removed from the equation as negligible since $I_B$ is $\leq 2 \times 10^{-9}$ amperes (A) over the sensing range and the resistance (R) of the substance being measured is $\leq 2 \times 10^4$ ohms, thus rendering $I_B \cdot R \leq 40$ μV, which is far less than kT/q. Equation (1) can therefore be re-written as equation (2a) and (2b):

$$I_C = I_o \exp\{q(V_B + \Psi_s - V_E)/kT\} \quad \text{Equation (2a):}$$

$$I_C = I_o \exp\{2.3(V_B + \Psi_s - V_E)/SS\} \quad \text{Equation (2b):}$$

Figure 10A:
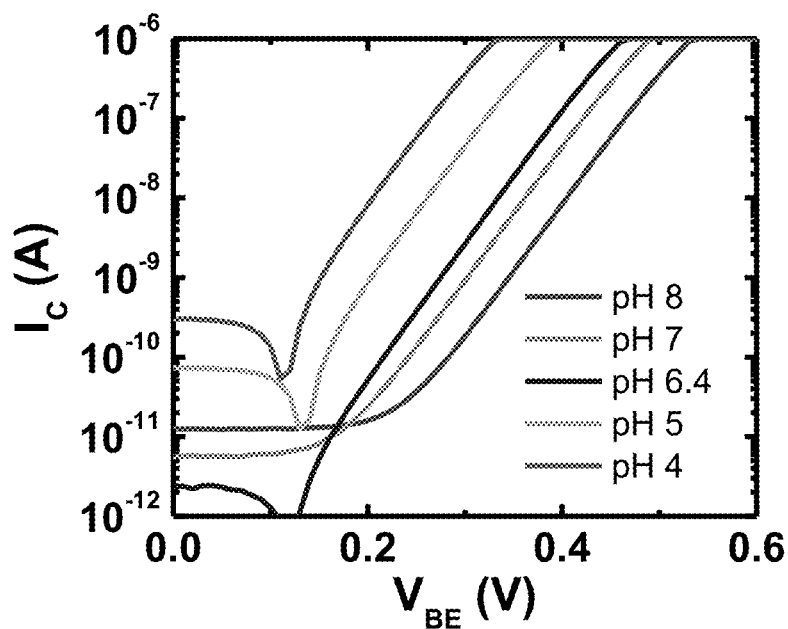
FIG. 10a depicts an example of a transfer curve describing the current of the collector ($I_c$) as a function of the difference ($V_{BE}$) at applied voltages measured at the reference electrode ($V_b$) and emitter ($V_e$) of a BJT for each calibration solution having a known pH.
Figure 10B:
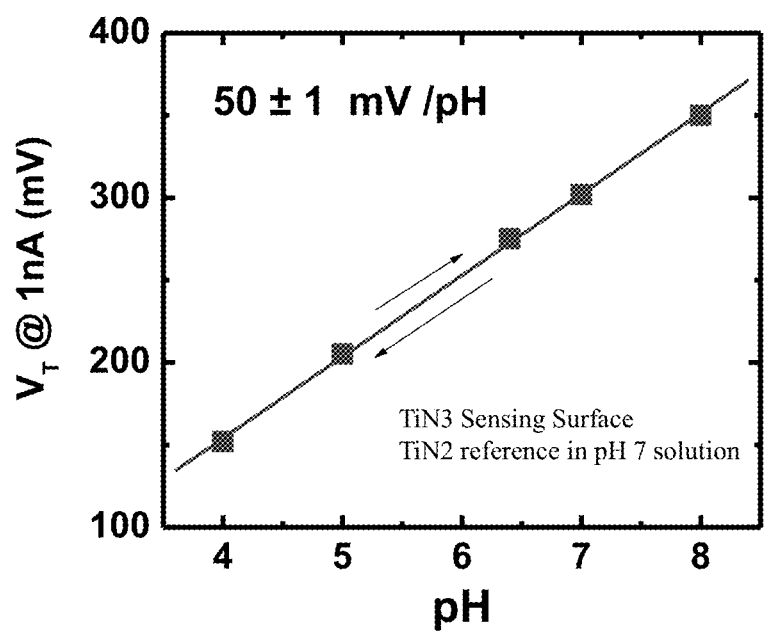
FIG. 10b depicts an example of a calibration curve plotting $V_{BE}$ as measured by the transfer curve of FIG. 10a at a selected $I_c$ of 1 Nano ampere (1 nA) as a function of pH for each of the calibration solutions.
Figure 11A:
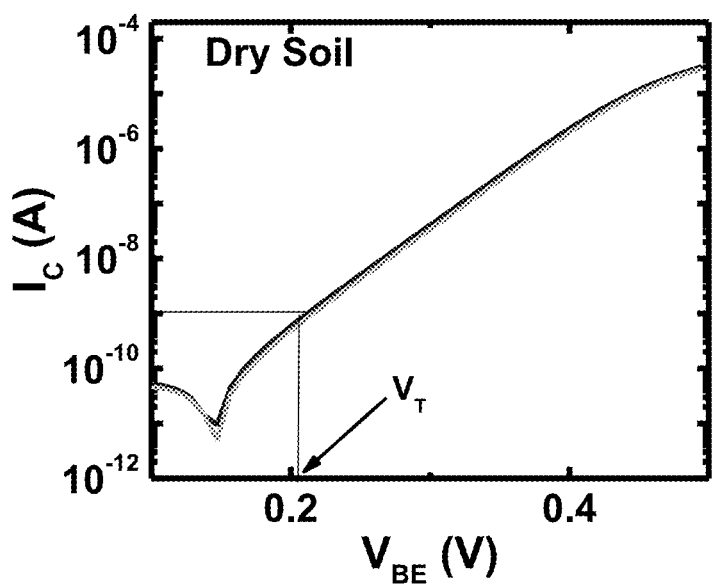
FIG. 11a depicts an example of an embodiment of a transfer curve for a dry soil of an unknown pH measured using an embodiment of a measuring device of the present disclosure.

The variable SS refers to the sub-threshold swing, wherein SS is defined as the change in the applied voltage $V_{BE}$ of the BJT, where $V_{BE} = V_B - V_E$, corresponding to a decade change in $I_C$ (i.e. a change from $1 \times 10^{-10}$ A to $1 \times 10^{-9}$ A to $1 \times 10^{-8}$ A, etc.). It can be surmised that SS=2.3 kT/q. An example of SS is shown in FIG. 10b, wherein the SS was calculated to be approximately 50±1 mV/pH. From Equation (2b) it can be observed that $I_c$ may depend exponentially on the surface potential $\Psi_s$ of the sensing surface 105. Since $\Psi_s$ depends on the surface charge density of the H+ ions, a change in charge density associated with bound H+ ions within a Debye length of the sensing surface 105 may cause the sensing current $I_C$ to vary and thus be a detectable signal to measure as output at the collector 421. As shown in FIGS. 10a, 11a, a transfer curve may be prepared by plotting the sensing current $I_C$ measured at the collector 421 as a function of the voltage $V_{BE}$ which may be calculated as the difference between the voltage applied to the reference electrode 106 at the wire 411 ($V_B$) and the voltage applied to the emitter 419 ($V_E$).

Using the measurements and voltages applied to the BJT, a transfer curve may be plotted for a plurality of calibration solutions having a known concentration of an analyte by plotting the $I_C$ measured at collector 421 as a function of the applied voltage $V_{BE}$ (measured as $V_B - V_E$). Subsequently, a calibration curve may be prepared from the transfer curve values, wherein values of $V_{BE}$ for each calibration solution may be plotted at a selected $I_C$ that is consistent for each calibration solution. The selected $I_C$ value may be plotted onto the calibration curve as a function of the known analyte concentrations of the calibration solutions. To find the unknown analyte concentrations of additional substances, measurements of $V_{BE}$ at the selected $I_C$ may be measured and plotted onto the calibration curve in order to identify the unknown analyte concentration. For example, if the calibration solutions were plotted onto the calibration curve at a $V_{BE}$ measured at $I_C$=1 nA as a function of a known analyte concentration, the $I_C$ selected for plotting the substance having an unknown analyte concentration onto the calibration curve will be the $V_{BE}$ measured at $I_C$=1 nA Likewise, if the $V_{BE}$ of the calibration curves are plotted at a $V_{BE}$ measured at $I_C$=3 nA, then the substance having an unknown analyte concentration will also be plotted onto the calibration curve using a $V_{BE}$ measured at $I_C$=3 nA.

Figure 4B:
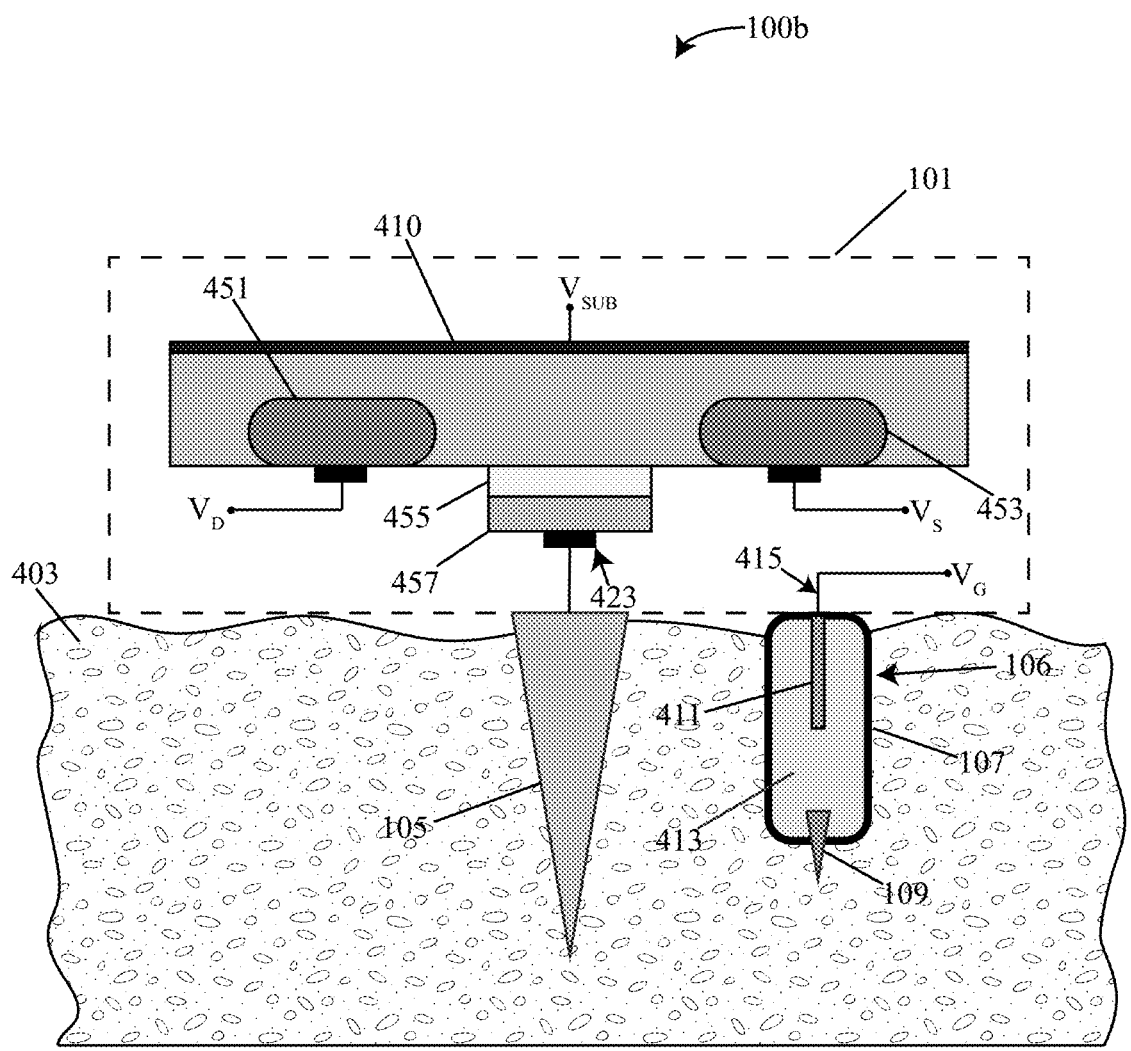
FIG. 4b depicts a schematic view of an embodiment of a sensor comprising a field effect transistor (FET)
Figure 5B:
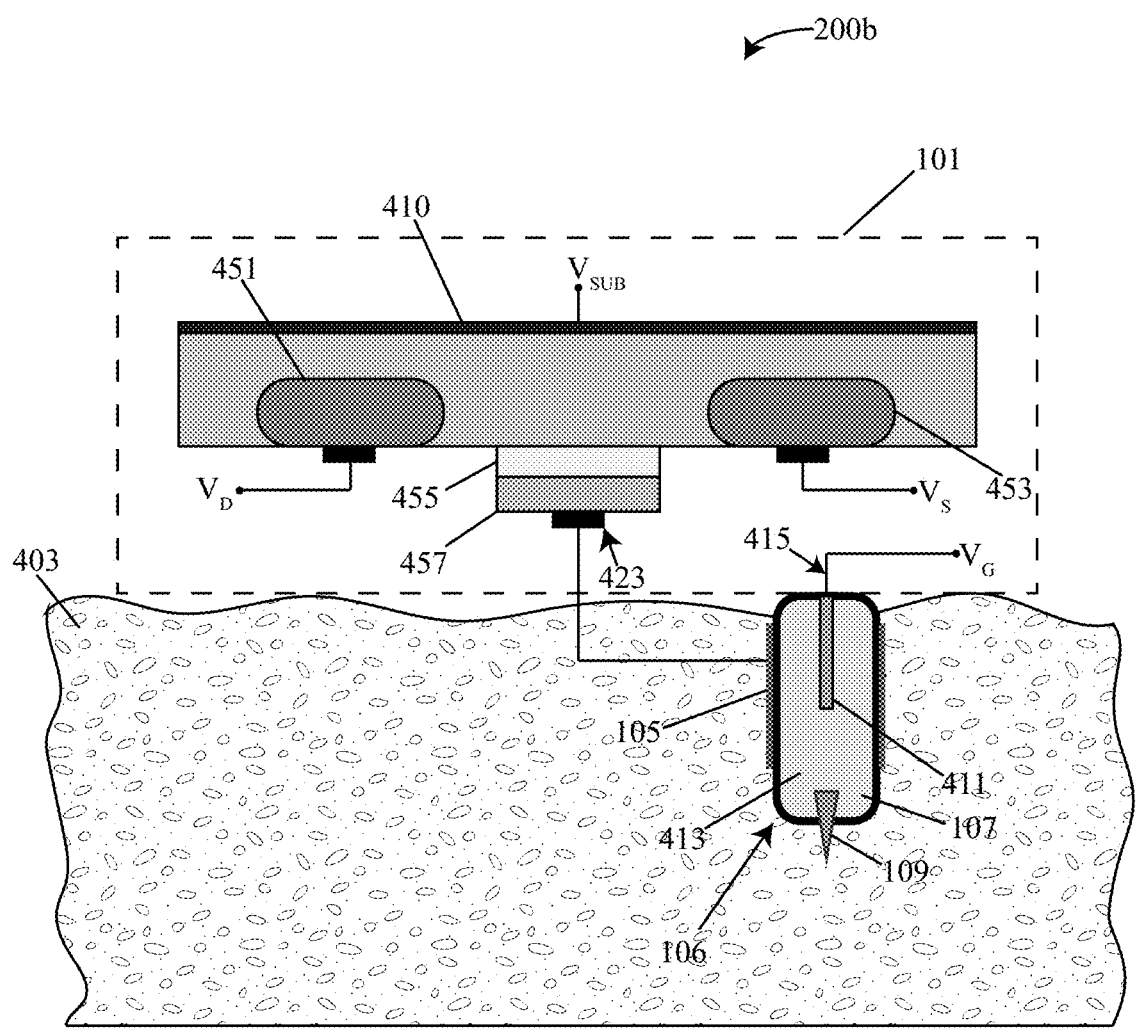
FIG. 5b depicts a schematic view of an alternative embodiment of a sensor comprising a FET.

In alternative embodiments of measuring device 100, 200, 300 which are referred to herein as measuring device 100b, 200b, 300b, the BJT transducer may be replaced with an FET transducer as pictured by the schematics of FIGS. 4b, 5b, 6b. Embodiments of the FET transducer may include a substrate 410 which may be a silicon substrate or doped silicon substrate 410, one or more oxide layers 455, a gate 457 electrically connected to the sensing surface 105, a source 453 and a drain 451. Embodiments of the oxide layer(s) 455 may include an insulating material that may be sensitive to changes in analyte concentrations, such as a change in pH. In some embodiments of the FET transducer, the oxide layer(s) 455 may include hafnium (IV) oxide ($HfO_2$), silicon dioxide ($SiO_2$), aluminum oxide ($Al_2O_3$), vanadium (V) oxide ($V_2O_5$), titanium dioxide ($TiO_2$), tungsten (III, IV, or V) oxide and combinations of oxide layer(s) 455 thereof.

Embodiments of the drain 451 and source 453 can comprise any materials that may be conventionally used for creating FET transducers, as known by a person skilled in the art and may be formed by conventional methods as known and understood. For example, the drain 451 and source 453 may be formed using an epitaxial growth process to deposit a crystalline layer onto the substrate 410 of the FET transducer. The epitaxial silicon, silicon, germanium, and/or carbon-doped silicon (Si:C) can be doped during the deposit of the substrate 410 by adding a dopant or impurity to form a silicide. Depending on the type of FET transistor desired, the drain 451 and source 453 may be doped with an n-type dopant or a p-type dopant. In alternative embodiments, the drain 451 and source 453 may be doped with boron. The drain 451 and the source 453 may be positioned on each side of the gate 457 as depicted in FIGS. 4b, 5b, 6b.

Embodiments of the measuring device 100b, 200b, 300b utilizing an FET as the transducer may operate by measuring current ($I_D$) at the drain 451 as the sensing signal (analogous to the sensing signal $I_C$ at the collector 421 of the BJT). Measurements of $I_D$ may be made by setting the voltage applied to the wire 411 of the reference electrode 106 equal to a gate voltage $V_G$, where $V_G$ may be >0V. The gate voltage, $V_G$ may be varied or held constant, in a manner analogous to the voltage applied to the emitter $V_E$ of a BJT. The voltage applied to the drain 451 ($V_D$) may be a low voltage, approximately 10-50 mV while the voltage applied to the substrate 410 ($V_{SUB}$) and the voltage applied to the source 453 ($V_S$) may be held constant, for example, in the exemplary embodiment $V_{SUB}$ and $V_S$ may be set to 0V. Similar to the BJT transducer, a transfer curve may be plotted using the measurements of $I_D$ at the drain 451 of the FET transducer as a function of the gate voltage ($V_G$) applied at the wire 411 of the reference electrode 106. Subsequently, a calibration curve may be prepared by plotting a transfer curve for a plurality of calibration solutions having known concentrations of an analyte being measured. From the transfer curve, the values of $V_G$ at a selected $I_D$ (e.g. 1 nA) may be plotted onto the calibration curve as a function of the known analyte concentration of the calibration solutions. Subsequently, measurements of $V_G$ at the same selected $I_D$ (e.g. 1 nA) may be measured for substances of unknown analyte concentration and plotted onto the calibration curve in order to identify the unknown analyte concentration of the substance.

System for Measuring pH

Figure 7A:
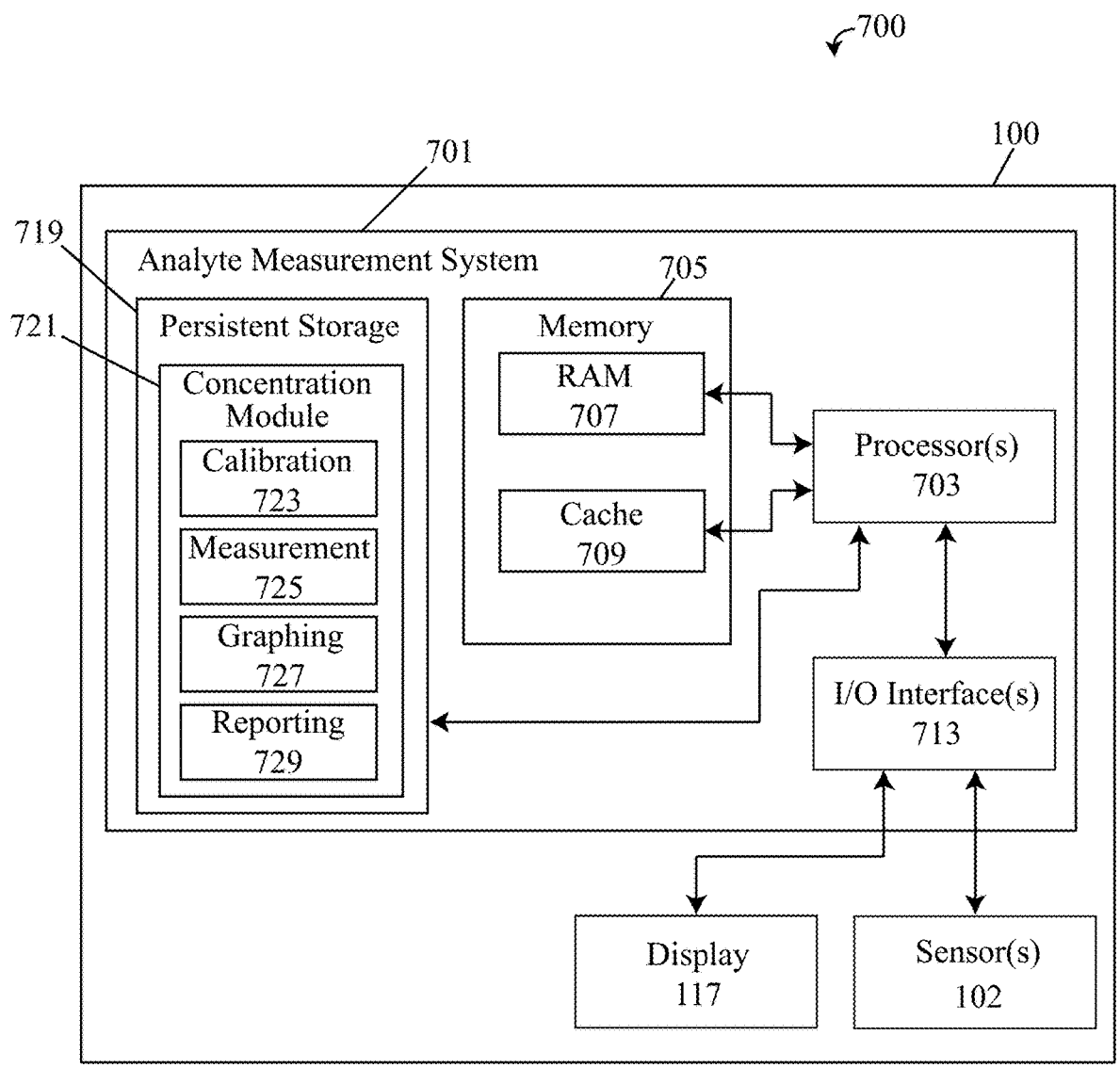
FIG. 7a depicts a functional block diagram describing an embodiment of a measuring device comprising an analyte measurement system.
Figure 7B:
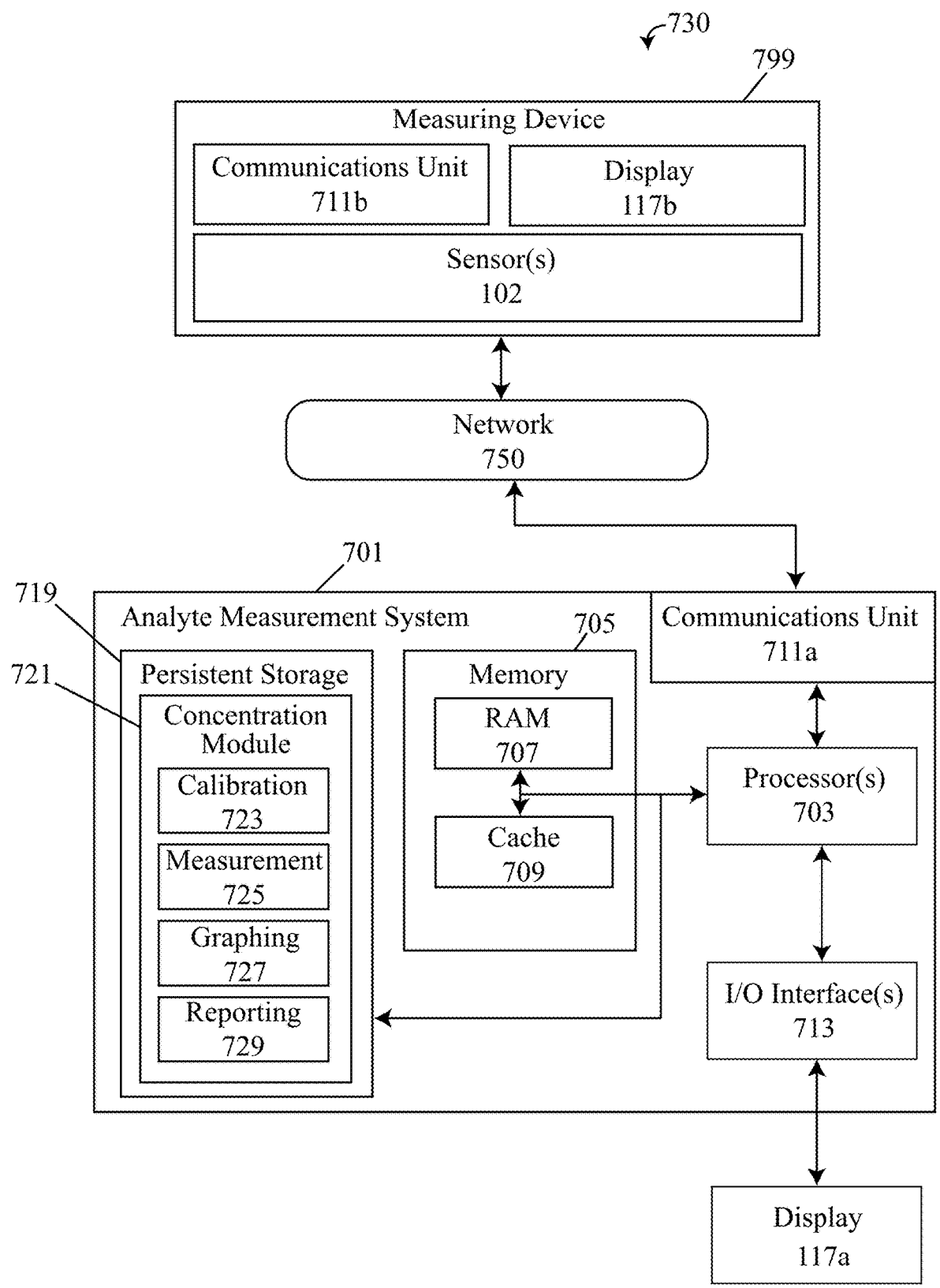
FIG. 7b depicts a functional block diagram describing an alternative embodiment of a measuring device connected to an analyte measurement system via a computer network.

Referring to the drawings, FIGS. 7a-7b depict a functional block diagram of a computing environment 700, 730 capable of measuring an analyte concentration in accordance with the embodiments of the present disclosure. Computing environment 700 may include one or more embodiments of a measuring device 100, 200, 300, 100*b*, 200*b*, 300*b* housing an analyte measurement system 701, display 117 and sensor(s) 102. The term sensor(s) 102 may refer to the combination of the transducer, the sensing surface 105, and the reference electrode 106.

Figure 9:
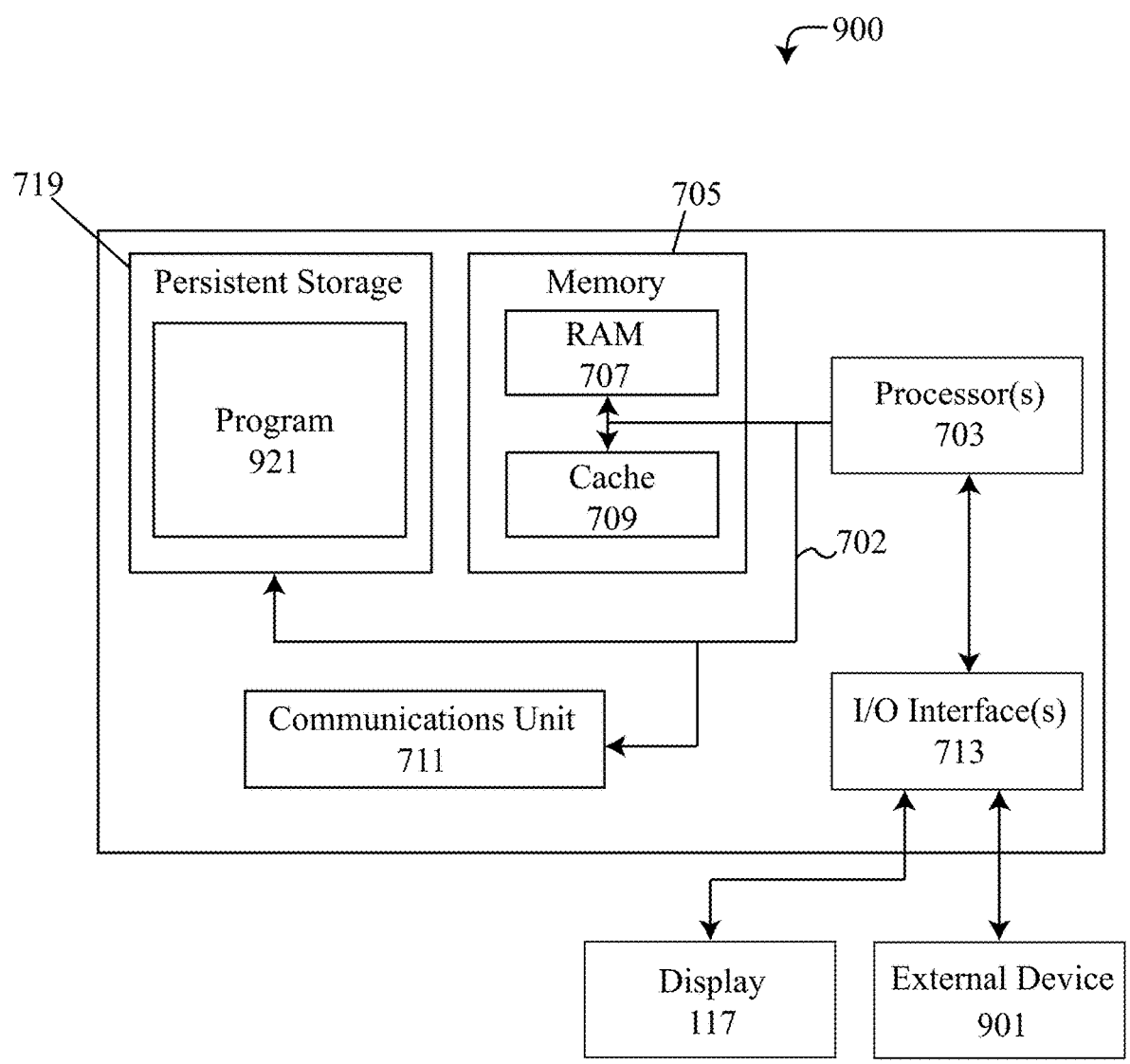
FIG. 9 depicts an embodiment of a block diagram of internal and external components of a computer system in accordance with the embodiments of the present disclosure.

In alternative embodiments, computer environment 730 may interconnect the analyte measurement system 701, display 117 and sensor(s) 102 of the measuring devices 100, 200, 300, 100*b*, 200*b*, 300*b*, 799 via a computer network 750. Embodiments of the measuring devices 100, 200, 300, 100*b*, 200*b*, 300*b*, 799, sensors 102 and/or analyte measurement system 701, may each be a specialized computer system comprising specialized configurations of hardware, software or a combination thereof as depicted in FIGS. 1-7*b* of the present disclosure and in embodiments described herein. Embodiments of the measuring devices 100, 200, 300, 100*b*, 200*b*, 300*b*, 799, sensors 102 and/or analyte measurement system 701 may not only comprise the elements of the systems and devices depicted in FIGS. 1-7*b* but may also incorporate one or more elements of a computer system 900 as shown in FIG. 9 and described in the COMPUTER SYSTEM section detailed below. One or more elements of the computer system 900 may be integrated into the specialized computer systems of the computing environment 700, 730 including the measuring devices 100, 200, 300, 100*b*, 200*b*, 300*b*, 799, analyte measurement system 701 and sensor(s) 102.

Embodiments of the measuring devices 100, 200, 300, 100*b*, 200*b*, 300*b*, 799 and analyte measurement system 701 may be desktop computers, laptop computers, tablet computers, smartphones, mobile computing devices, server computers, or any other computer system known in the art. In some embodiments, measuring devices 100, 200, 300, 100*b*, 200*b*, 300*b*, 799, analyte measurement system 701 and sensor(s) 102 may represent computer systems utilizing clustered computers and components to act as a single pool of seamless resources when accessed through network 750. For example, such embodiments may be used in data center, cloud computing, storage area network (SAN), and network attached storage (NAS) applications. In certain embodiments, measuring devices 100, 200, 300, 100*b*, 200*b*, 300*b*, 799, measurement system 701 and sensor(s) 102 may represent virtual machines. In general, measuring devices 100, 200, 300, 100*b*, 200*b*, 300*b*, 799, analyte measurement system 701 and sensor(s) 102 may be representative of any electronic devices, or combination of electronic devices, capable of executing machine-readable program instructions, as described in greater detail with regard to FIGS. 8*a*-8*b*.

Embodiments of the measuring devices 100, 200, 300, 100*b*, 200*b*, 300*b*, 799, analyte measurement system 701 and sensor(s) 102 may each be connected and placed into communication with one another over a computer network 750. Embodiments of the computer network 750 may be constructed using wired, wireless or fiber optic connections. As shown in the exemplary embodiments, the measuring devices 100, 200, 300, 100*b*, 200*b*, 300*b*, 799, analyte measurement system 701 and sensor(s) 102 may connect and communicate over the network 750 using a communication unit 711 (i.e. communication units 711*a*, 711*b* shown in FIG. 7*b*) such as a network interface controller or other network communication hardware. Embodiments of the communication unit 711 may implement specialized electronic circuitry allowing for communication using a specific physical layer and a data link layer standard. For example, Ethernet, Fiber channel, Wi-Fi or Token Ring.

Communication unit 711 may further allow for a full network protocol stack, enabling communication over network 750 to the group of computer systems or other computing hardware devices linked together through communication channels. The network 750 may facilitate communication and resource sharing among the measuring devices 100, 200, 300, 100*b*, 200*b*, 300*b*, 799, analyte measurement system 701 and sensor(s) 102 and additional hardware devices connected to the network 750, for example a network accessible storage media. Examples of network 750 may include a local area network (LAN), home area network (HAN), wide area network (WAN), back bone networks (BBN), peer to peer networks (P2P), campus networks, enterprise networks, the Internet, cloud computing networks and any other network known by a person skilled in the art.

Embodiments of the analyte measurement system 701 may include a concentration module 721. The term "module" may refer to a hardware module, software module, or a module may be a combination of hardware and software resources. A module (whether hardware, software or a combination thereof) may be designed to implement or execute one or more specific tasks, routines or functions. Embodiments of hardware-based modules may include self-contained components such as chipsets, sensors, specialized circuitry, one or more memory 705 devices and/or persistent storage 719. A software-based module may be part of a program 921, program code or linked to program code containing specific programmed instructions loaded into a memory 705 or persistent storage 719 of a computer system operating in computing environment 700, 730.

Embodiments of the concentration module 721, whether hardware, software, or a combination thereof, may perform the functions and tasks associated with calibrating sensor(s) 102 which may include the transducer connected to a sensing surface 105, a reference electrode 106 comprising a non-porous enclosure 107, a wire 411 submerged within in a reference solution 413 as well as a metallic plug 109 which may extend outwardly from inside the non-porous enclosure 107. Other tasks or functions of the concentration module 721 may include measuring the sensing current ($I_C$ or $I_D$) being outputted from an attached transducer at either the collector 421 of a BJT or a drain 451 of an FET and the applied voltages $V_{BE}$ or $V_G$. Embodiments of the concentration module 721 may perform calculation functions such as graphing operations to plot or obtain concentration values of analytes for each unknown substance based on the applied voltage and current measurements and plotting the measurements onto a calibration curve of known analyte concentrations to identify the concentration of the analyte present in the substance being measured. Embodiments of the concentration module 721 may further display or generate reports and/or graphics describing analyte measurements of for each substance, which may be logged or displayed to users of the analyte measurement system 701 and/or measuring devices 100, 200, 300, 100*b*, 200*b*, 300*b*, 799.

In the exemplary embodiments of the computing environment 700, 730 depicted in FIGS. 7*a*-7*b*, the concentration module 721 may be integrated into the analyte measurement system 701. However, in alternative embodiments of the computing environment 700, 730, the concentration module 721 may be integrated into one or more computer systems of the computing environment 700, 730, such as the sensor(s) 102. Embodiments of the concentration module 721 may comprise one or more sub-modules which may perform one or more of the specific functions or tasks of the concentration module 721. In some embodiments, the sub-modules of the concentration module 721 may include a calibration module 723, measurement module 725, graphing module 727 and/or a reporting module 729.

Embodiments of the calibration module 723 may perform the task or function of calibrating the sensor(s) 102 using one or more calibration solutions having a known concentration of the analyte being measured. Embodiments of the calibration module 723 may request and allow for user input of calibration data, including the type of calibration solution, temperature of the calibration solutions, the analyte being measured and the concentration of analyte present in each calibration solution. Embodiments of the calibration module 723 may automate the calibration process and generation of the calibration curve. The calibration module may initiate the sensor(s) 102 measurements of the transducer current ($I_C$ or $I_D$) being outputted as the sensing signal for each calibration solution and set each of the voltages being applied to the transducer during the calibration measurements of the sensing signal ($I_C$ or $I_D$). Moreover, embodiments of the calibration module 723 may receive and store the calibration data of the sensing signal ($I_C$ or $I_D$) and the voltages applied to the transducer during the calibration period for each calibration solution having a known analyte concentration. Embodiments of the calibration module 723, may transmit the measurements of the sensing signal ($I_C$ or $I_D$), voltages applied to the transducer during calibration and the known analyte concentration of the calibration solutions to the graphing module 727 for further processing of the collected measurements into a transfer curve and/or calibration curve.

Embodiments of the concentration module 721 may further comprise a measurement module 725 which may perform the task or function of automating the process of collecting measurement data from the sensor(s) 102 for each substance measured having an unknown analyte concentration. The measurement module 725 may set one or more voltages being applied to the transducer and measure the current being outputted as the sensing signal from the collector 421 or drain 451 (depending on the transducer being used). Embodiments of the measurement module 725 may receive and store the measurements of the current outputted as the sensing signal ($I_C$ or $I_D$) as well as the store data describing the voltages applied to each component of the sensor(s) 102.

Embodiments of the concentration module 721 may include a graphing module 727 which may be tasked with performing the function of transforming the current, voltage and concentration data collected by the calibration module 723 and measurement module 725 into one or more transfer curves and/or calibration curves. Referring to the drawings, FIG. 10a depicts an example of a plurality of transfer curves generated from data collected from a BJT transducer. As seen in FIG. 10a, each of the transfer curves having a known H+ ion concentration measured as a pH, may be plotted by graphing the sensing signal (current $I_C$) measured in amperes (A) as function of the $V_{BE}$ in volts (V) being applied to the BJT. From the transfer curve data, a calibration curve may be plotted by the graphing module 727 as shown in FIG. 10b. Embodiments of the calibration curve may plot $V_T$ as a function of the known analyte concentration of H+ ions, (measured as a pH in this example) for each calibration solution, wherein $V_T$=the $V_{BE}$ measured at a consistently selected $I_C$ for each calibration solution, for example 1 nA (i.e., 1×10−9 A) as shown in FIG. 10b.

Figure 11B:
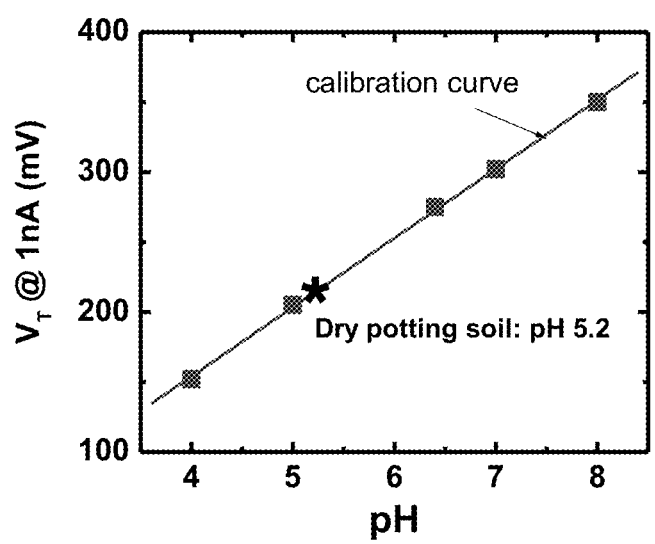
FIG. 11b depicts a calculated $V_T$ of the dry soil of FIG. 11a plotted onto the calibration curve of FIG. 10b.

Embodiments of the graphing module 727 may subsequently plot the $V_T$ for each substance having an unknown analyte concentration onto the calibration curve previously created to identify the corresponding known concentrations of the analyte of the calibration solutions. FIG. 11a depicts an example of a transfer curve generated from transducer measurements taken from a soil sample having an unknown pH. As shown in FIG. 11a, a transfer curve is graphically generated by plotting $I_C$ measurements of the collector 421 as a function of the applied voltage $V_{BE}$. The selected $V_T$ (1 nA) is derived from the transfer curve as shown at approximately 0.21V (~210 mV). The graphing module 727 may subsequently plot the 210 mV measurement onto the calibration curve of FIG. 10b, as shown in FIG. 11b, to identify the pH of the soil as having a pH of approximately 5.2.

Embodiments of the concentration module 721 may also include a reporting module 729. Embodiments of the reporting module 729 may perform the task or function of displaying or presenting the concentrations of analytes for the substances being measured, to the user of the analyte measurement system 701. For example, the reporting module 729 may display the pH or concentration of the analyte being measured, in the appropriate units, on display 117 as shown by the example in FIGS. 1-3. In alternative embodiments, the reporting module 729 may graphically display the graph generated the graphing module 727 or a variation thereof using a graphical user interface (GUI) of the analyte measurement system 701 to display the information via the display 117.

FIG. 7b depicts an alternative computing environment 730. The computing environment 730 may differ from computing environment 700 by delocalizing the system comprising the sensor(s) 102 from the analyte measurement system 701. Embodiments of the measuring device 799 may incorporate one or more components of a computer system 900 alongside the sensor(s) 102. However, instead of communicating within a single device as shown in FIG. 7a which integrates the analyte measurement system 701 and sensor(s) 102 in a single enclosure, the sensor(s) 102 may be integrated into a measuring device 799 that is separated from the concentration module 721. Embodiments of the measurement system 701 and the concentration module 721 may communicate over network 750 to automate and collect data from the sensor(s) 102 and subsequently plot the transfer curves, calibration curves and identify the concentration of unknown analytes for each of the tested substances. The results of the analyte measurements may be reported and displayed by either the analyte measurement system 701 via display 117 and/or the display 117b of the measuring device 799.

Method for Measuring Analyte Concentration

Figure 8A:
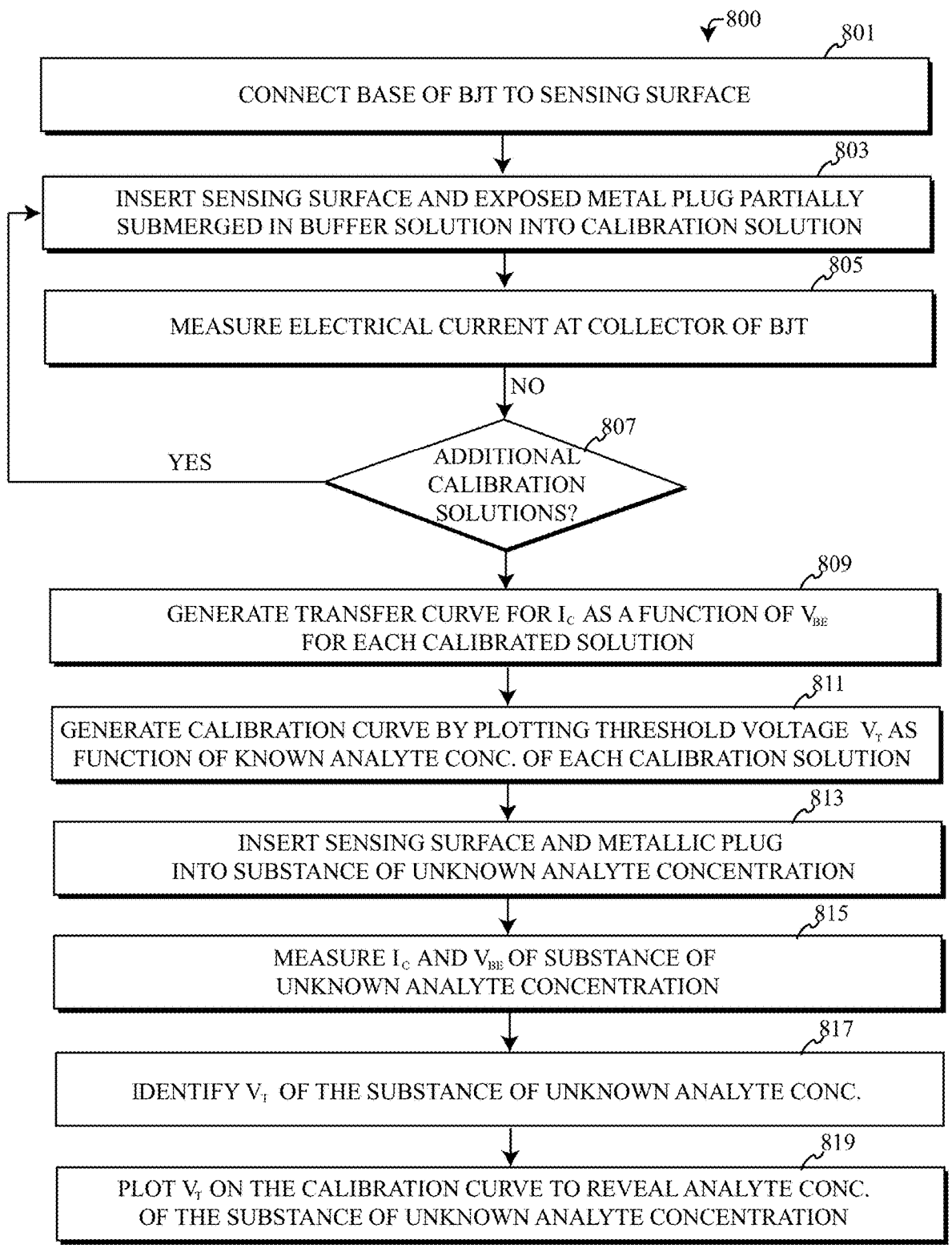
FIG. 8a depicts a flowchart illustrating an embodiment of a method for measuring an unknown analyte concentration.
Figure 8B:
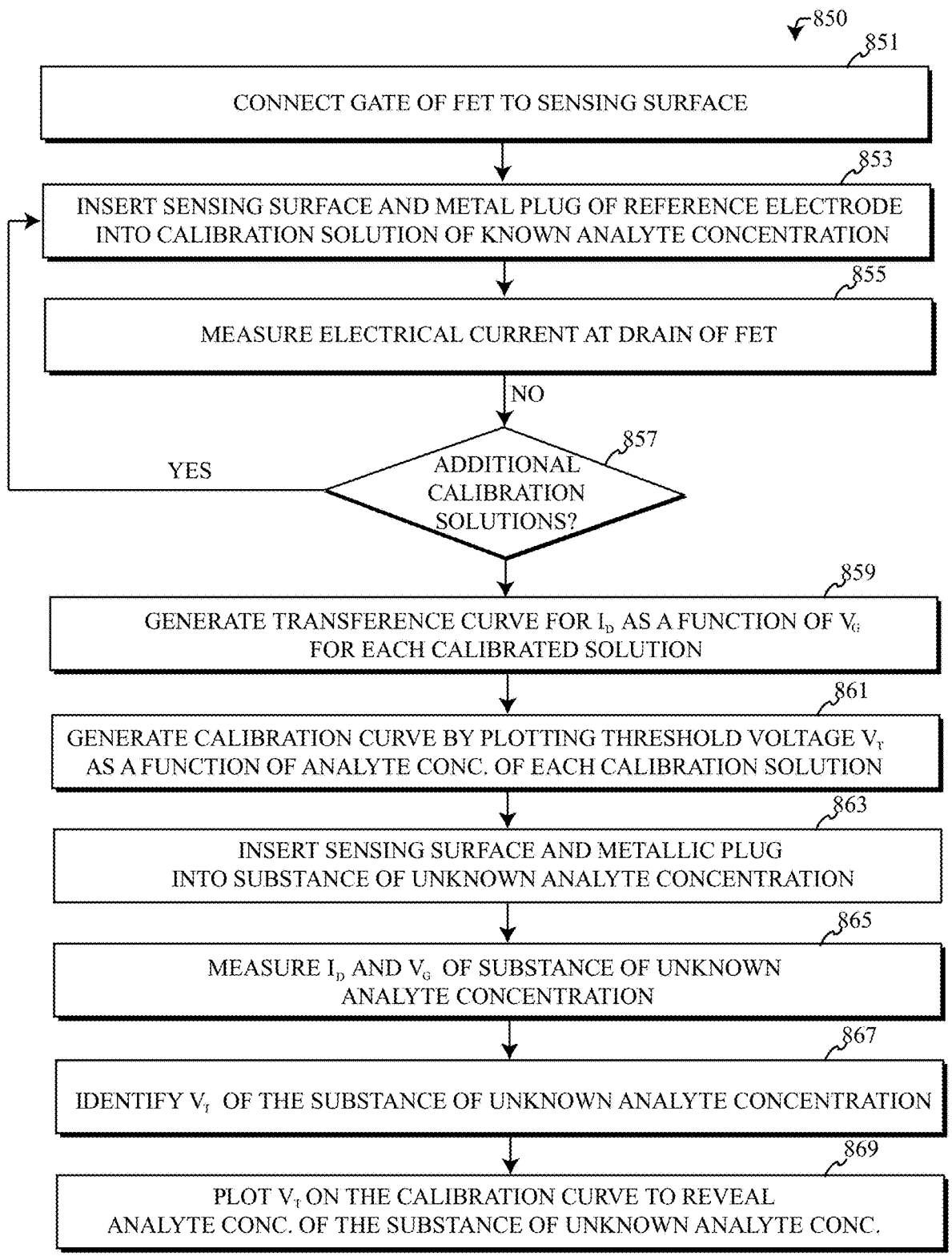
FIG. 8b depicts a flowchart illustrating an alternative embodiment of a method for measuring an unknown analyte concentration.

The drawings of FIGS. 8a-8b represent embodiments of methods for measuring the concentration of analytes with measuring devices 100, 200, 300, 100b, 200b, 300b, 799 and/or the computing environment 700, 730 described in FIGS. 1-7b, using one or more computer systems as defined generically by computer system 900 in FIG. 9 below and more specifically by the embodiments of specialized computer systems depicted in FIGS. 1-7b. A person skilled in the art should recognize that the steps of the methods described in FIG. 8a-8b may be performed in a different order than presented and the methods of FIG. 8a-8b may not require all the steps described herein to be performed. Rather, some embodiments may alter the methods by using one or more of the steps discussed below.

FIG. 8a is a flowchart illustrating a method 800 for measuring analyte concentration, in accordance with the embodiments of the present disclosure. The embodiment of the method 800 may begin at step 801. In step 801, a base 417 of a BJT may be connected to a sensing surface 105 using a conductive material 415, extending from a terminal 423 of the base 417 to the sensing surface 105. In some embodiments of method 800, a power supply may also be connected to a wire 411 of the reference electrode 106, housed within a non-porous enclosure 107 by making a connection between the power supply and the wire 411 using a conductive material 415.

In step 803, a sensing surface 105 connected to the base 417 in step 801 may be inserted into a calibration solution having a known analyte concentration. An exposed portion of a metallic plug 109 that may be partially submerged within a reference solution 413, may also be inserted into the calibration solution along with a non-porous enclosure 107 of the reference electrode 106 in some embodiments. Voltages for the BJT may be set by a user of the measuring device 100, 200, 300, 100b, 200b, 300b, 799 using a control system 104 or automatically as programmed by a concentration module 721 operating as part of an analyte measurement system 701. In some embodiments, the voltage $V_B$ applied to the wire 411 of the reference electrode 106 and the voltage $V_C$ applied to the collector 421 may be initially set to 0V or held constant at a selected voltage. The voltage $V_E$ applied to the emitter 419 may be held at a constant voltage or a variable voltage, as set by the user or the calibration module 723.

In step 805 of method 800, the collector 421 of the BJT may output an electrical current, $I_C$ in response to the voltages applied in step 803 to each region of the BJT and wire 411 of the reference electrode 106. In step 805, the current $I_C$ being outputted by the collector 421 may be measured and recorded to a memory 705 or stored within a persistent storage 719 device. For example, by storing the measurements of $I_C$ within the calibration module 723. In step 807, a determination may be made to determine whether or not the sensing surface 105 or the reference electrode 106 should be inserted into any additional plurality of calibration solutions in order to measure the current $I_C$ of the collector 421 for the voltages being applied to the BJT. If, in step 807, additional calibration solutions are scheduled to be measured, the method 800 may return to step 803 and repeat steps 803-807 until each of the calibration solutions that will form the calibration curve have been measured. Conversely, if in step 807, there is a determination made that there are not any additional calibration solutions to measure, the method may proceed to step 809.

In step 809 of method 800, a transfer curve may be generated from the measurements of each calibration solution. To generate the transfer curve from the calibration solutions, the current, $I_c$, that was measured and/or recorded in step 805 for each calibration solution may be calculated and/or plotted as a function of the applied voltage $V_{BE}$ of the BJT, wherein the applied voltage $V_{BE}=(V_B-V_E)$. Step 809 may be repeated until a transfer curve for each calibration solution has been generated, as depicted by the exemplary embodiment of FIG. 10a. Embodiments of the transfer curve may be generated in some instances by an analyte measurement system 701 and more specifically, a graphing module 727 of the analyte measurement system 701.

In step 811 of method 800, A calibration curve may be generated. Embodiments of the calibration curve may be created using the measurements of the transfer curve generated in step 809 in combination with the known concentrations of the analyte being measured in each calibration solution. The calibration curve may plot $V_T$ for each calibration solution as a function of the known analyte concentration of the calibration solutions. The value for each $V_T$ being plotted may be defined as the $V_{BE}$ value at a consistently selected $I_C$. For example, in FIG. 10b an $I_C$ of 1 nA ($1 \times 10^{-9}$ A) was consistently selected to plot each calibration solution. As shown in the example of FIG. 10b, each plot point created by the $V_T$ identified for each calibration solution plotted may be connected together to form a calibration curve.

Embodiments of method 800 may continue on from step 811 to step 813. In step 813, the sensing surface 105, the metallic plug 109 of the reference electrode 106 and in some embodiments, the non-porous enclosure 107 may be inserted into a substance having an unknown analyte concentration. Similar to step 803 above, in step 813, the voltages for $V_B$ and $V_C$ may be set to a constant voltage (such as 0V) while the voltage $V_E$ being applied to the emitter 419 may held at a constant voltage or varied by a user or as programmed by the analyte measurement system 701. As the voltages are applied, measurements of the sensing signal, current $I_C$, measured at the collector 421 and the voltage $V_{BE}$ applied to the BJT may be recorded and saved to a memory 705 or persistent storage 719 in step 815 of method 800. Moreover, the measurements of $I_C$ and $V_{BE}$ obtained in step 815 may be used to generate a transfer curve for the substance having an unknown analyte concentration, wherein the $I_C$ is plotted at a function of the $V_{BE}$. FIG. 11a depicts an example of a transfer curve created from measurements of a dry soil having an unknown pH.

In step 817 of method 800, the transfer curve may be used to identify a $V_T$ of the substance having an unknown analyte concentration. The value of the $V_T$ of the substance being measured may be extracted from the transfer curve created in step 815 described above. The $V_T$ may be identified as the value of $V_{BE}$ at the $I_C$ previously selected in step 811 to plot the calibration curve (i.e., 1 nA as described by the example above). FIG. 11a depicts an example of a $V_T$ being identified from a transfer curve generated for a dry soil having an unknown pH. As shown in FIG. 11a, the $V_T$ of the dry soil having an unknown pH was measured to be approximately 0.21V or 210 mV. In step 819, the $V_T$ identified in step 817 may be plotted onto the calibration curve created in step 811 to reveal the unknown analyte concentration. FIG. 11b depicts an example of plotting the dry soil of FIG. 11a onto a calibration curve. $V_T=210$ mV is plotted onto the calibration curve where the Y-axis reads 210 mV as shown in the figure. The pH of the dry soil can be extrapolated from the calibration curve by following the plotted point for the dry soil down to the x-axis which is labelled as pH in this example because it is measuring the concentration of the H+ ion as the analyte. In the example of FIG. 11b, the pH is shown to be measured as approximately 5.2. The inventors confirmed the measurement of the pH in the experimental results displayed by FIGS. 11a-11b using litmus paper. In the experiment, the accuracy of their measurement was confirmed by a litmus paper reading of a pH of approximately 5.

Figure 14:
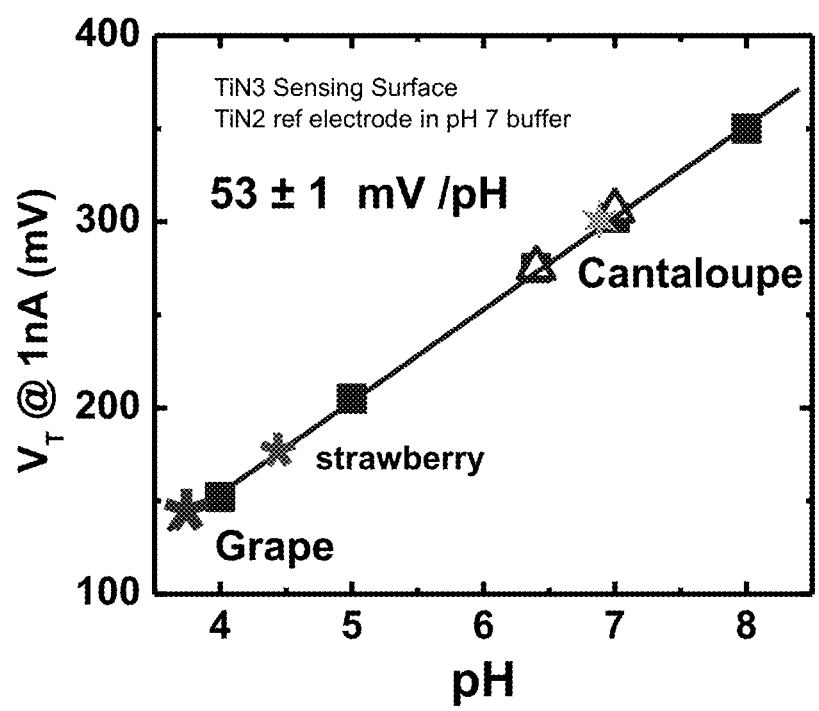
FIG. 14 depicts a graphical interpretation of experimental results describing the analyte measurements (pH) of a plurality of fruits plotted onto the calibration curve of FIG. 10b.

In an alternative experiment, the inventors of the present disclosure applied an embodiment of the measuring device 300, 300b and method 800, 850 to measure the pH of a plurality of fruits. The experimental results are depicted in FIG. 14 and Table 1 below. The experiments were performed using a sensing surface 105 constructed out of $TiN_3$, a reference electrode containing a wire 411 constructed out of $TiN_2$ in a reference solution having a pH of 7 and a metallic plug 109 constructed out of tungsten. Measurements of $I_c$ and $V_{BE}$ were taken for a plurality of fruits in situ and a transfer curve for each fruit was prepared from the $I_c$ and $V_{BE}$. $V_T$ for each fruit was selected where $I_C=V_{BE}$ at 1 nA and plotted onto a calibration curve as shown in FIG. 14, wherein the calibration curve was generated using calibration solutions having known pHs. Results were subsequently verified for accuracy against known pHs for each fruit as recorded and publicly accessible in the scientific literature. The pH measurements for each of the fruits and the reference pHs are provided in Table 1 below.

TABLE 1 pH Sensing of Fruits

| Fruit | pH (sensor) | Literary pH |
|---|---|---|
| Grape | 3.72 | ~2.9-3.8 |
| Strawberry | 4.5 | ~3-4 |
| Cantaloupe | 6.9 | ~6-8 |

Figure 12A:
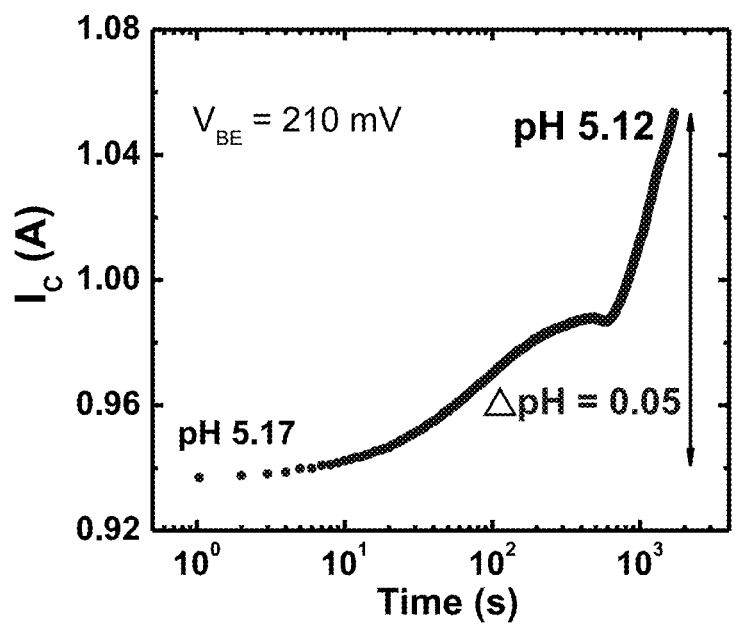
FIG. 12a depicts a graphical interpretation of experimental results measuring an in-situ time dependence of an analyte measurement (pH) of a dry soil.

Embodiments of the experimental example provided by FIGS. 11a-11b also confirmed that the overall pH readings of the dry soil varied very little over the time and continue to be accurate, allowing for the proposed devices, systems and methods of the present disclosure to be affixed within a substance or medium such as soil, slurries, crops such as fruit, patients, or animals for an extended period of time (i.e. continuous monitoring of an analyte concentration without having to remove the measuring device 100, 200, 300, 100b, 200b, 300b, 799). As exemplified by FIG. 12a, the pH of the dry soil was measured at a fixed $V_{BE}$ of 210 mV over a 1×10³ seconds (1000 seconds or 16.67 mins). The variation of the dry soil pH (ΔpH) readings varied by 0.05, providing evidence that the proposed method 800 is capable of continuously measuring analytes such as H+ concentration with a high resolution and without malfunctioning or becoming clogged and inaccurate. The measurements were confirmed using litmus paper to test the pH.

Figure 12B:
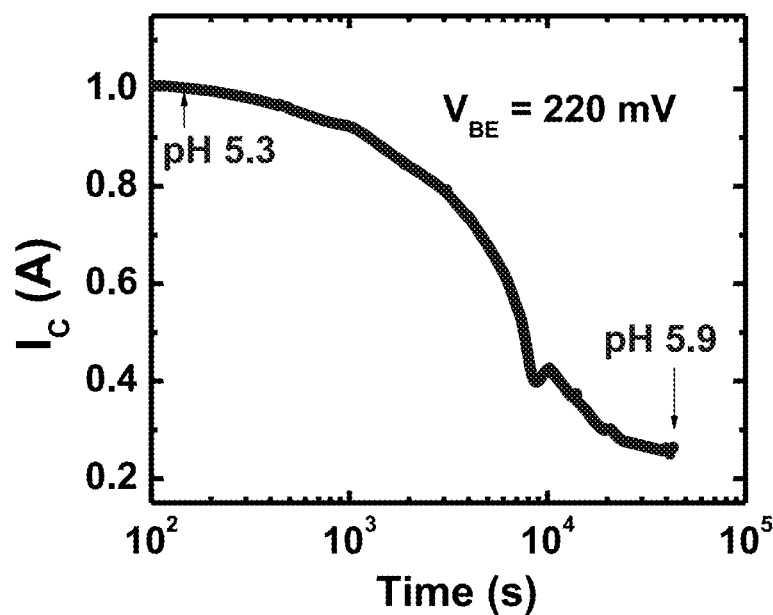
FIG. 12b depicts a graphical interpretation of experimental results measuring an in-situ time dependence of an analyte measurement (pH) of wet soil.

A second variation of the experiment was performed using wet soil which accurately tracked variations in the pH occurring in nearly real-time, as various salts in the wet soil dissolved over time. As exemplified in FIG. 12b, a wet soil being monitored for pH was measured for pH using a constant $V_{BE}$ of 220 mV and monitored for approximately 24 hours. Over the course of the 24-hour period, the pH was continuously sampled as shown by the graph of FIG. 12b. At the first sampling period, the pH was measured to be approximately 5.3, while at the end of the 24-hour monitoring period, the pH was measured to be approximately 5.9. Litmus paper samples were used to verify the pH at the beginning of the experiment and at the end of the experiment to ensure accuracy. Colored indications of the litmus paper confirmed that the pH at the start of the 24 hour period to be approximately a pH of 5 and the color of the litmus paper at the end of the 24 hour experiment confirmed the pH to be approximately 6, coinciding with the measurements of the experiment shown in FIG. 12b, further confirming the accuracy of the proposed methods, devices and systems described herein for the application of monitoring analyte concentrations of soil and within other substances in-situ and over extended periods of time.

Figure 13:
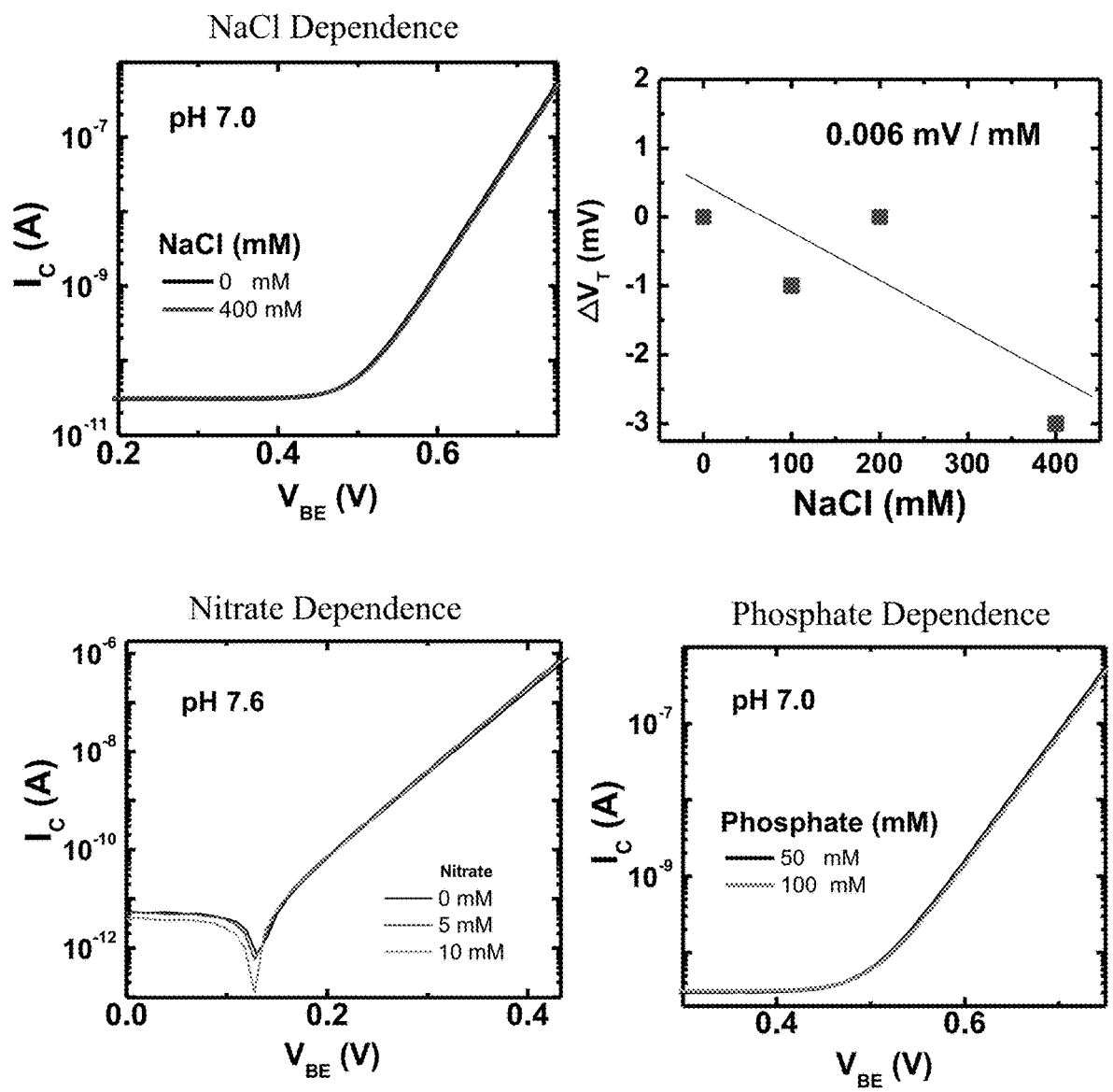
FIG. 13 depicts graphical interpretations of experimental results describing the minimal interference of Na+, Cl−, $(NO_3)^-$, and $(PO_4)^{-3}$ ions on the analyte measurements of pH obtained by embodiments of the sensor of the present disclosure.

Further experimentation was performed to confirm selectivity toward the analytes being measured by method 800 and the corresponding devices and systems used to implement method 800 are not impacted by one or more additional ions or analytes that may be present. As shown in FIG. 13, experimentation performed by the inventors confirmed that concentrations of ions common to soil, such as Na, Cl, nitrate and phosphate have minimal impact on the accuracy of the systems, methods and devices described in this application when measuring H+ concentration. For example, the changes in the measurements of $V_T$ as a function of the concentration of NaCl concentration was incredibly low. Measurements were taken using samples having a concentration of NaCl between 0 mM to 400 mM. As shown by FIG. 13, the transfer curves of the 0 mM NaCl and 400 mM NaCl samples are nearly identical, overlapping almost entirely. In fact, the change in $V_T$ ($\Delta V_T$) was approximately 0.006 mV/mM (6 μV/mM). Similar findings are depicted in FIG. 13 for the dependence on nitrate and phosphate concentrations. As shown, the concentration on nitrates tested between 0 mM to 10 mM and the concentration of phosphates tested between 50 mM to 100 mM resulted in transfer curves that partially or completely overlap, indicating little to no interference on the $I_C$ and $V_{BE}$ measurements obtained while implementing method 800 to measure H+ concentrations as the analyte.

FIG. 8b is a flowchart illustrating an alternative embodiment of a method 850 for measuring analyte concentration, in accordance with the embodiments of the present disclosure. The embodiment of the method 850 may begin at step 851. In step 851, a gate 457 of a FET may be connected to a sensing surface 105 using a conductive material 415, extending from a terminal 423 of the gate 457 to the sensing surface 105. In some embodiments of method 850, a power supply may also be connected to a wire 411 of a reference electrode 106. The wire 411 housed within a non-porous enclosure 107 may be connected to the power supply by making a connection between the power supply and the wire 411 using a conductive material 415.

In step 853, a sensing surface 105 connected to the gate 457 in step 851 may be inserted into a calibration solution having a known analyte concentration. An exposed portion of a metallic plug 109 may be inserted into the calibration solution along with a non-porous enclosure 107. An enclosed portion of the metallic plug 109 may be partially submerged within a reference solution 413. Voltages for the FET may be set by a user of the measuring device 100, 200, 300, 100b, 200b, 300b, 799 using a control system 104 or automatically as programmed by a concentration module 721 operating as part of an analyte measurement system 701. In some embodiments, the voltage $V_G$ applied to the reference electrode 106 may be held at a constant voltage or a variable voltage, as set by the user or the calibration module 723. The voltage $V_s$ applied to the source 453 and the voltage $V_{SUB}$ applied to the substrate 410 may be initially set to a voltage of 0V or another desired constant voltage. The voltage $V_D$ applied to the drain 451 may be a small voltage, which may be approximately 10-50 mV in some embodiments.

In step 855 of method 850, the drain 451 of the FET may output an electrical current, $I_D$ in response to the voltages applied in step 853 to each region of the FET and the wire 411 of the reference electrode 106. In step 855, the current $I_D$ being outputted by the drain 451 may be measured and recorded to a memory 705 or stored within a persistent storage 719 device. For example, by storing the measurements of $I_D$ within the calibration module 723. In step 857, a determination may be made to determine whether or not the sensing surface 105 and metallic plug 109 of the reference electrode 106 should be inserted into any additional plurality of calibration solutions in order to measure the current $I_D$ of the drain 451 for the voltages being applied to the FET. If, in step 857, additional calibration solutions are scheduled to be calibrated, the method 850 may return to step 853 and repeat steps 803-807 until each of the calibration solutions that will form the calibration curve have been measured. Conversely, if in step 857, there is a determination made that there are not any additional calibration solutions to measure, the method may proceed to step 859.

In step 859 of method 850, a transfer curve may be generated from the measurements of each calibration solution. To generate the transfer curve from the calibration solutions, the current $I_D$ that was measured and/or recorded in step 855 for each calibration solution may be calculated and/or plotted as a function of the applied voltage $V_G$ of the FET. Step 859 may be repeated until a transfer curve for each calibration solution has been generated, similar to the transfer curves depicted by in FIG. 10a which were performed using a BJT transducer. Embodiments of the transfer curve may be generated in some instances by an analyte measurement system 701 and more specifically, a graphing module 727 of the analyte measurement system 701.

In step 861 of method 850, a calibration curve may be generated. Embodiments of the calibration curve may be created using the measurements of the transfer curve generated in step 859 in combination with the known concentration of analyte for each calibration solution. The calibration curve may plot $V_T$ for each calibration solution as a function of the known analyte concentrations of the calibration solutions. The value for each $V_T$ being plotted using a FET transducer may be defined as the $V_G$ value for a consistently selected $I_D$ for each calibration solution. Each plot point created by the $V_T$ identified for each calibration solution plotted may be connected together to form a calibration curve.

Embodiments of method 850 may continue on from step 861 to step 863. In step 863, the sensing surface 105 and the reference electrode 106 may be inserted into a substance having an unknown analyte concentration. Similar to step 853 described above, in step 863, the voltages for $V_S$ and $V_{SUB}$ may be set to a constant voltage (such as 0V), the voltage of the drain 451 may be set to a small voltage of approximately 10-50 mV while the voltage $V_G$ being applied to the wire 411 of the reference electrode 106 may be held at a constant voltage or varied voltage set by a user or as programmed by the analyte measurement system 701. As the voltages are applied, measurements of the sensing signal (current $I_D$) measured at the drain 451 and the voltage $V_G$ may be recorded and saved to a memory 705 or persistent storage 719 in step 865 of method 850. Moreover, the measurements of $I_D$ and $V_G$ obtained in step 865 may be used to generate a transfer curve for the substance having an unknown analyte concentration, wherein the $I_D$ is plotted as a function of the $V_G$.

In step 867 of method 850, the transfer curve may be used to identify a $V_T$ of the substance having an unknown analyte concentration. The value of the $V_T$ of the substance being measured may be extracted from the transfer curve created in step 865 described above. The $V_T$ when using an FET transducer may be identified as the value of $V_G$ at the $I_D$ consistently selected in step 861 to create the calibration curve. In step 869, the $V_T$ identified in step 867 may be plotted onto the calibration curve created in step 861 to reveal the analyte concentration of the substance being measured, in a manner similar to the method shown by FIG. 11b. FIG. 11b depicts an example of plotting the dry soil of FIG. 11a onto a calibration curve. $V_T$=210 mV is plotted onto the calibration curve where the Y-axis reads 210 mV as shown in the figure. The pH of the dry soil can be extrapolated from the calibration curve by following the plotted point for the dry soil down to the x-axis which is labelled as pH. In the example of FIG. 11b, the pH is shown to be measured as approximately 5.2. The inventors confirmed the measurement of the pH in the experimental results displayed by FIGS. 11a-11b using litmus paper. In the experiment, the accuracy of their measurement was confirmed by a litmus paper reading of a pH of approximately 5.

Computer System

FIG. 9 is a block diagram of internal and external components of a computer system 900, which may be representative of the one or more computer systems depicted by measuring devices 100, 200, 300, 100b, 200b, 300b of FIGS. 1-6a and/or the computing environment 700, 730 as shown in FIGS. 7a-7b, in accordance with the embodiments of the present disclosure. It should be appreciated that FIG. 9 provides only an illustration of one implementation and does not imply any limitations with regard to the environments in which different embodiments may be implemented. In general, the components illustrated in FIG. 9 are representative of any electronic device capable of executing machine-readable program instructions. Examples of computer systems, environments, and/or configurations that may be represented by the components illustrated in FIG. 9 include, but are not limited to, personal computer systems, server computer systems, thin clients, thick clients, laptop computer systems, tablet computer systems, cellular telephones (e.g., smart phones), multiprocessor systems, microprocessor-based systems, network PCs, minicomputer systems, mainframe computer systems, and distributed cloud computing environments that include any of the above systems or devices.

Computer system 900 may include communications fabric 702, which provides for communications between one or more processors 703, memory 705, persistent storage 719, communications unit 711, and one or more input/output (I/O) interfaces 713. Communications fabric 702 can be implemented with any architecture designed for passing data and/or control information between processors (such as microprocessors, communications and network processors, etc.), system memory 705, external devices 901, and any other hardware components within a system. For example, communications fabric 702 can be implemented with one or more buses.

Memory 705 and persistent storage 719 may be computer-readable storage media. Embodiments of memory 705 may include random access memory (RAM) 707 and cache memory 709. In general, memory 705 can include any suitable volatile or non-volatile computer-readable storage media. Software, such as a program 921 may be stored in persistent storage 719 for execution and/or access by one or more of the respective processors 703 via one or more devices of memory 705. Such software programs 921 can include a concentration module 721, calibration module 723, measurement module 725, graphing module 727 and reporting module 729.

Persistent storage 719 may include, for example, a plurality of magnetic hard disk drives. Alternatively, or in addition to magnetic hard disk drives, persistent storage 719 can include one or more solid state hard drives, semiconductor storage devices, read-only memories (ROM), erasable programmable read-only memories (EPROM), flash memories, or any other computer-readable storage media that is capable of storing program instructions or digital information. Embodiments of the media used by persistent storage 719 can also be removable. For example, a removable hard drive can be used for persistent storage 719. Other examples include optical and magnetic disks, thumb drives, and smart cards that are inserted into a drive for transfer onto another computer-readable storage medium that is also part of persistent storage 719.

Communications unit 711 (including communications unit 711*a*, 711*b*) provides for communications with other computer systems or devices via a network (e.g., network 750). In this exemplary embodiment, communications unit 711 may include network adapters or interfaces such as a TCP/IP adapter cards, wireless Wi-Fi interface cards, 3G, 4G, or 5G wireless interface cards or other wired or wireless communication links. The network can comprise, for example, copper wires, optical fibers, wireless transmission, routers, firewalls, switches, gateway computers and/or edge servers. Software and data used to practice embodiments of the present invention can be downloaded to measuring devices 100, 200, 300, 100*b*, 200*b*, 300*b*, analyte measurement system 701, computer systems operating in computing environment 700, 730 or computer system 900 through communications unit 711 (e.g., via the Internet, a local area network or other wide area network). From communications unit 711, the software and data can be loaded onto persistent storage 719.

One or more I/O interfaces 713 may allow for input and output of data with other devices that may be connected to computer system 900. For example, I/O interface 713 can provide a connection to one or more external devices 901 such as sensor(s) 102, keyboard, computer mouse, touch screen, virtual keyboard, touch pad, pointing device, or other human interface devices. External devices 901 can also include portable computer-readable storage media such as, for example, thumb drives, portable optical or magnetic disks, and memory cards. I/O interface 713 may also connect to display 117. Display 117 provides a mechanism to display data to a user and can be, for example, a computer monitor or screen. Display 117 can also be an incorporated display and may function as a touch screen, such as a built-in display of a tablet computer.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration but are not intended to be exhaustive or limited to the embodiments disclosed. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments disclosed herein.

What is claimed is:

1. A device comprising:
    a transducer encased within a moisture-proof enclosure;
    a sensing surface electrically connected to the transducer, the sensing surface extending exterior to the moisture-proof enclosure; and
    a reference electrode, wherein the reference electrode comprises a sealed, non-porous enclosure, a reference solution encased within the non-porous enclosure, a wire submerged in the reference solution and a metallic plug partially enclosed within the non-porous enclosure wherein said metallic plug partially extends exterior to the non-porous enclosure.

2. The device of claim 1, wherein the transducer is a bipolar junction transistor (BJT) comprising an emitter, base and collector with the sensing surface electrically connected to the base of the BJT.

3. The device of claim 1, wherein the sensing surface or the wire of the reference electrode is comprised of titanium nitride (TiN) or a TiN coating.

4. The device of claim 1, wherein the metallic plug is constructed out of a material or coated with a material selected from the group consisting of tungsten, titanium nitride, platinum, and silver chloride coated silver.

5. The device of claim 1, wherein the metallic plug has a surface area extending exterior to the non-porous enclosure that is at least 25 times smaller than a surface area of the metallic plug enclosed within the non-porous enclosure.

6. The device of claim 1, wherein the reference solution is a pH buffer solution having a pH of at least 7.

7. The device of claim 1, wherein the sensing surface is deposited on at least one exterior sidewall of the non-porous enclosure of the reference electrode.

8. A device comprising:
    a reference electrode having a sealed, non-porous enclosure, a reference solution encased within the non-porous enclosure, a wire submerged in the reference solution and a metallic plug partially enclosed within the non-porous enclosure, wherein said metallic plug partially extends exterior to the non-porous enclosure.

9. The device of claim 8, wherein the wire of the reference electrode is comprised of titanium nitride (TiN) or a TiN coating.

10. The device of claim 8, wherein the metallic plug is constructed out of a material or coated with a material selected from the group consisting of tungsten, titanium nitride, platinum, silver and silver chloride.

11. The device of claim 8, wherein the metallic plug has a surface area extending exterior to the non-porous enclosure that is at least 25 times smaller than a surface area of the metallic plug enclosed within the non-porous enclosure.

12. A method for measuring an analyte concentration comprising the steps of:
    connecting, a base of a bipolar junction transistor (BJT) encased in a moisture-proof enclosure to a sensing surface extending exterior to the moisture-proof enclosure;
    inserting, the sensing surface and a metallic plug of a reference electrode into a plurality of calibration solutions each having a known analyte concentration, wherein said reference electrode comprises a non-porous enclosure, a reference solution encased within the non-porous enclosure, a wire submerged in a reference solution and the metallic plug is partially extends exterior to the non-porous enclosure;
    measuring an electrical current outputted from a collector ($I_c$) of the BJT as a function of a change in a difference between a voltage applied to the reference electrode ($V_B$) and a voltage applied to an emitter ($V_E$) of the BJT, wherein the $V_B$ is 0 volts (V) and $V_E$ is <0V, for each of the plurality of calibration solutions;
    generating a transference curve plotting $I_c$ as a function of the change in $V_B$-$V_E$ ($V_{BE}$) for each of the plurality of calibration solutions;
    creating a calibration curve plotting $V_{BE}$ at a selected $I_c$ for each of the plurality of calibration solutions as a function of the known analyte concentration of each of the plurality of calibration solutions;
    measuring the $I_c$ of a substance of unknown analyte concentration outputted at the collector of the BJT; and
    plotting the $V_{BE}$ of the substance of unknown analyte concentration on the calibration curve at the selected $I_C$ used to create the calibration curve.

13. The method of claim 12, wherein at least one of the sensing surface and the wire of the reference electrode is comprised of titanium nitride (TiN) or a TiN coating, and the metallic plug is constructed out of a material or coated with a material selected from the group consisting of tungsten, titanium nitride, platinum, silver chloride coated silver.

14. The method of claim 12, wherein the metallic plug has a surface area extending exterior to the non-porous enclosure that is at least 25 times smaller than a surface area of the metallic plug partially enclosed within the non-porous enclosure.

15. The method of claim 12, wherein the reference solution is a buffer solution having a pH of at least 7.

16. A computer system comprising:
a processor;
a bipolar junction transistor (BJT) electrically coupled to the processor, said BJT is encased within a moisture-proof enclosure;
a sensing surface electrically connected to the BJT, the sensing surface extending exterior to the moisture-proof enclosure;
a reference electrode extending from the moisture-proof enclosure, wherein the reference electrode comprises a non-porous enclosure, a reference solution encased within the non-porous enclosure, a wire submerged the reference solution and a metallic plug partially enclosed within the non-porous enclosure and said metallic plug extending exterior to the non-porous enclosure; and
a computer-readable storage media coupled to a processor, wherein the computer readable storage media contains program instructions executing a computer-implemented method comprising the steps of:
measuring an electrical current outputted from a collector ($I_c$) of the BJT as a function of a change in a difference between a voltage applied to the reference electrode ($V_B$) and a voltage applied to an emitter ($V_E$) of the BJT, wherein the $V_B$ is 0 volts (V) and $V_E$ is <0V, for each of a plurality of calibration solutions;
generating a transference curve comparing $I_c$ as a function of the change in ($V_B$–$V_E$) (hereinafter "$V_{BE}$") for each of the plurality of calibration solutions;
creating a calibration curve plotting $V_{BE}$ at a selected $I_c$ for each of the plurality of calibration solutions as a function of a known analyte concentration of each of the plurality of calibration solutions;
measuring the $I_c$ of a substance having an unknown analyte concentration, outputted at the collector of the BJT; and
plotting the $V_{BE}$ of the substance having an unknown analyte concentration at the selected $I_c$ used to create the calibration curve.

17. The computer system of claim 16, wherein at least one of the sensing surface and the wire of the reference electrode is comprised of titanium nitride (TiN) or a TiN coating.

18. The computer system of claim 16, wherein the metallic plug is constructed out of a material or coated with a material selected from the group consisting of tungsten, titanium nitride, platinum, silver and silver chloride.

19. The computer system of claim 16, wherein the metallic plug has a surface area extending exterior to the non-porous enclosure that is at least 10 times smaller than a surface area of the metallic plug partially enclosed within the non-porous enclosure.

20. The computer system of claim 16, wherein the reference solution is a buffer solution having a pH of approximately 7 to 8.

21. A computer program product comprising:
one or more computer readable storage media having computer-readable program instructions stored on the one or more computer readable storage media, said program instructions executes a computer-implemented method comprising the steps of:
measuring an electrical current outputted by a collector ($I_c$) of a bipolar junction transistor (BJT) as a function of a change in a difference between a voltage ($V_B$) applied to a reference electrode comprising a non-porous enclosure, a reference solution encased within the non-porous enclosure and metallic plug partially enclosed within the non-porous enclosure and extending exterior to the non-porous enclosure and a voltage applied to an emitter ($V_E$) of the BJT, said difference measured using a sensing surface connected to a base of the BJT, and the metallic plug partially extending from the non-porous enclosure of the reference electrode inserted into each of a plurality of calibration solutions;
generating a transference curve comparing $I_c$ as a function of the change in ($V_B$–$V_E$) (hereinafter "$V_{BE}$") for each of the plurality of calibration solutions;
creating a calibration curve plotting $V_{BE}$ at a selected $I_c$ for each of the plurality of calibration solutions as a function of a known analyte concentration of each of the plurality of calibration solutions;
measuring the $I_c$ of the substance of unknown analyte concentration outputted at the collector of the BJT using the sensing surface and the metallic plug of the reference electrode inserted into the substance of unknown analyte concentration; and
plotting the $V_{BE}$ of the substance of unknown analyte concentration at the selected $I_c$ used to create the calibration curve.

22. The computer program product of claim 21, wherein the sensing surface is comprised of titanium nitride (TiN) or a TiN coating.

23. The computer program product of claim 21, wherein the metallic plug is constructed out of a material or coated with a material selected from the group consisting of tungsten, titanium nitride, platinum, silver and silver chloride.

24. The computer program product of claim 21, wherein the metallic plug has a surface area extending from the non-porous enclosure is at least 10 times smaller than a surface area of the metallic plug enclosed within the non-porous enclosure.

25. The computer program product of claim 21, wherein the reference solution is a buffer having a pH of at least 7.

* * * * *